United States Patent
Saji et al.

(10) Patent No.: US 10,828,380 B2
(45) Date of Patent: Nov. 10, 2020

(54) CONJUGATE OF POLYSARCOSINE AND NIR CONTRAST AGENT FOR PHOTOACOUSTIC IMAGING

(71) Applicant: CANON KABUSHIKI KAISHA, Tokyo (JP)

(72) Inventors: Hideo Saji, Kyoto (JP); Kohei Sano, Kyoto (JP); Akira Makino, Kyoto (JP); Kengo Kanazaki, Yokohama (JP); Fumio Yamauchi, Yokohama (JP); Satoshi Ogawa, Yokohama (JP); Tatsuki Fukui, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/762,251

(22) PCT Filed: Sep. 23, 2016

(86) PCT No.: PCT/JP2016/078966
§ 371 (c)(1),
(2) Date: Mar. 22, 2018

(87) PCT Pub. No.: WO2017/057653
PCT Pub. Date: Apr. 6, 2017

(65) Prior Publication Data
US 2018/0280547 A1    Oct. 4, 2018

(30) Foreign Application Priority Data

Sep. 30, 2015 (JP) ................................. 2015-194334
Feb. 9, 2016 (JP) ................................. 2016-022505

(51) Int. Cl.
| | |
|---|---|
| A61K 49/22 | (2006.01) |
| C08G 69/48 | (2006.01) |
| C08G 69/04 | (2006.01) |
| C08G 69/10 | (2006.01) |
| A61K 49/00 | (2006.01) |

(52) U.S. Cl.
CPC ........ *A61K 49/221* (2013.01); *A61K 49/0032* (2013.01); *A61K 49/0054* (2013.01); *C08G 69/04* (2013.01); *C08G 69/10* (2013.01); *C08G 69/48* (2013.01); *A61K 49/0019* (2013.01)

(58) Field of Classification Search
None
See application file for complete search history.

(56) References Cited

U.S. PATENT DOCUMENTS

| | | |
|---|---|---|
| 9,138,492 B2 | 9/2015 | Fukui et al. |
| 9,592,307 B2 | 3/2017 | Yamauchi et al. |
| 9,675,715 B2 | 6/2017 | Takahashi et al. |
| 9,750,827 B2 | 9/2017 | Miki et al. |
| 2012/0052011 A1 | 3/2012 | Fukui et al. |
| 2012/0052017 A1 | 3/2012 | Kato et al. |
| 2012/0225992 A1* | 9/2012 | Shalati ............... C08G 18/4669 524/507 |
| 2016/0067359 A1 | 3/2016 | Fukui et al. |
| 2016/0279271 A1 | 9/2016 | Yamauchi et al. |
| 2017/0224850 A1 | 8/2017 | Ogawa et al. |
| 2017/0333575 A1 | 11/2017 | Kondo et al. |
| 2018/0228922 A1 | 8/2018 | Saji et al. |

FOREIGN PATENT DOCUMENTS

| | | |
|---|---|---|
| EP | 2 305 214 A1 | 4/2011 |
| JP | 2012-520856 A | 9/2012 |
| JP | 2014-185312 A | 10/2014 |
| WO | 2009/148121 A1 | 12/2009 |
| WO | 2010/106169 A1 | 9/2010 |
| WO | 2014/013730 A1 | 1/2014 |
| WO | 2016/060277 A1 | 4/2016 |
| WO | 2016/143017 A1 | 9/2016 |

OTHER PUBLICATIONS

Arun Sreekumar et al., "Metabolomic Profiles Delineate Potential Role for Sarcosine in Prostate Cancer Progression," 457 Nature 910-914 (Feb. 2009).

Hiroki Tanisaka et al., "Near-Infrared Fluorescent Labeled Peptosome for Application to Cancer Imaging," 19(1) Bioconjugate Chem. 109-117 (Dec. 2007) (XP055047210).

Juliane Ulbricht et al., "On the Biodegradability of Polyethylene Glycol, Polypeptoids and Poly(2-oxazoline)s," 35(17) Biomaterials 4848-4861 (Jun. 2014) (XP055241156).

Robert Luxenhofer et al., "Polypeptoids: A Perfect Match for Molecular Definition and Macromolecular Engineering?" 51(13) J. Polym. Sci., Part A: Polym. Chem. 2731-2752 (Apr. 2013) (XP002765265).

(Continued)

Primary Examiner — James W Rogers
(74) Attorney, Agent, or Firm — Venable LLP

(57) ABSTRACT

An object is to provide a polymer having a high tumor/blood ratio. The present invention provides a polymer represented by the following formula (P1):

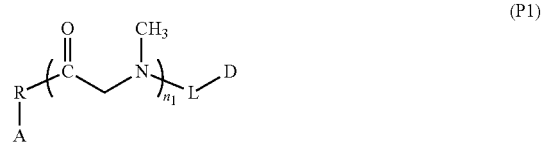

wherein in the formula (P1), R represents any of a residue derived from a polymerization initiator, or a functional group; A may not be present, and when present, A represents any of a low-molecular compound, a dye, a reporter molecule, a target-binding molecule, a polymer or D; L represents a linker and L may not be present; $n_1$ represents an integer of 1 or more; and D represents a dye backbone of a dye having absorption in the near-infrared region.

6 Claims, 6 Drawing Sheets

(56) References Cited

OTHER PUBLICATIONS

Masahiko Sisido et al., "Molecular Weight Distribution of Polysarcosine Obtained by NCA Polymerization," 178 Makromol. Chem. 3107-3114 (1977) (XP002765266).

S.G. Waley et al., "The Kinetics of the Polymerization of Sarcosine Carbonic Anhydride," 199 Proceedings of Royal Society Serie A 499-517 (1949) (XP055329711).

Notice of Reasons for Refusal in Japanese Application No. 2016-022505 (dated Apr. 14, 2020).

Alexander Birke et al, "Polypeptoid-block-polypeptide Copolymers: Synthesis, Characterization, and Application of Amphiphilic Block Copolypept(o)ides in Drug Formulations and Miniemulsion Techniques," 15 Biomacromolecules 548-557 (2014).

Kristina Klinker et al., "Evaluating Chemical Ligation Techniques for the Synthesis of Block Copolypeptides, Polypeptoids and Block Copolypept(o)ides: A Comparative Study," 6 Polym. Chem. 4612-4623 (May 2015).

Saji et al., U.S. Appl. No. 15/511,898, filed Mar. 16, 2017.

* cited by examiner

CONJUGATE OF POLYSARCOSINE AND NIR CONTRAST AGENT FOR PHOTOACOUSTIC IMAGING

TECHNICAL FIELD

The present invention relates to a polymer, and a contrast agent for photoacoustic imaging, including the polymer.

BACKGROUND ART

A photoacoustic tomography (hereinafter, sometimes abbreviated as "PAT") apparatus is known as one apparatus for visualizing information in a living body. In measurement using the PAT apparatus, an image in which the substance distribution in an object to be measured is computed can be obtained by measuring the intensity and the time of generation of a photoacoustic signal emitted from a substance (optical absorber) that absorbs light in the object to be measured, in irradiation of the object to be measured with light.

For the optical absorber, any substance can be here used as long as the substance absorbs light and emits an acoustic wave in a living body. For example, a blood vessel or a malignant tumor in a human body can be adopted for the optical absorber. Besides, molecules of indocyanine green (hereinafter, sometimes abbreviated as "ICG") and the like can also be administered into a body and utilized as a contrast agent. ICG well absorbs light in the near-infrared wavelength region, the light having a small influence in irradiation of a human body therewith and having a high permeability to a living body, and therefore can be suitably used as a contrast agent (sometimes abbreviated as a "photoacoustic contrast agent") in the PAT apparatus. In the present description, ICG refers to a compound represented by a structure of the following formula.

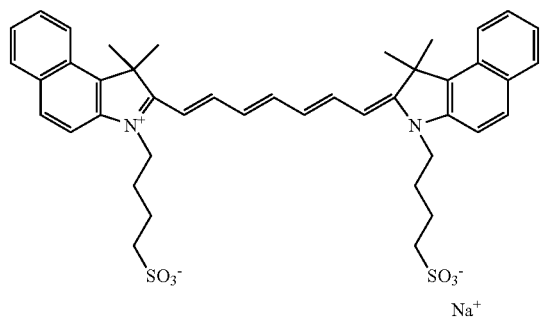

Herein, the counter ion may not be Na$^+$, and any counter ion such as H$^+$ or K$^+$ can be used. It is known that ICG has a very short half-life of about several minutes in blood.

PTL 1 reports an example in which a tumor accumulation is confirmed using a contrast agent in which polyethylene glycol (hereinafter, sometimes abbreviated as "PEG") is covalently conjugated with a near-infrared dye. The near-infrared dye can be conjugated to PEG to thereby allow the half-life in blood to be prolonged as compared with a single near-infrared dye.

CITATION LIST

Patent Literature

PTL 1: Japanese Patent Application Laid-Open No. 2012-520856

Non Patent Literature

NPL 1: Nature, (2009), 457, 910-914

SUMMARY OF INVENTION

Technical Problem

While the near-infrared dye-conjugated PEG disclosed in PTL 1 exhibits a high tumor accumulation property, the dye-conjugated PEG also has a high retentivity in blood, and therefore has the problem of being low in tumor/blood ratio.

Then, an object of the present invention is to provide a polymer having a high tumor/blood ratio, and a contrast agent for photoacoustic imaging, including the polymer.

Solution to Problem

The present invention provides a polymer represented by the following formula (P1).

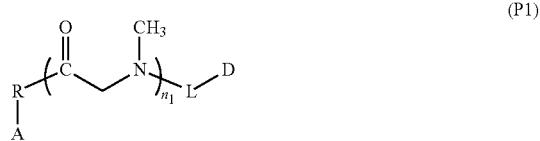

wherein in the formula (P1), R represents any of a residue derived from a polymerization initiator, or a functional group; A may not be present, and when present, A represents any of a low-molecular compound, a dye, a reporter molecule, a target-binding molecule, a polymer or D; L represents a linker and L may not be present; $n_1$ represents an integer of 1 or more; and D represents a dye backbone of a dye having absorption in the near-infrared region.

Further features of the present invention will become apparent from the following description of exemplary embodiments with reference to the attached drawings.

BRIEF DESCRIPTION OF DRAWINGS

FIGS. 2A and 2B represent the results at 10 and 24 hours after administration, respectively.

FIG. 7A illustrates cellular uptake study in culturing at 37° C. or 4° C. for 1 or 6 hours, and FIG. 7B illustrates inhibition assay in cellular uptake study using various inhibitors.

DESCRIPTION OF EMBODIMENTS

Figure 1:
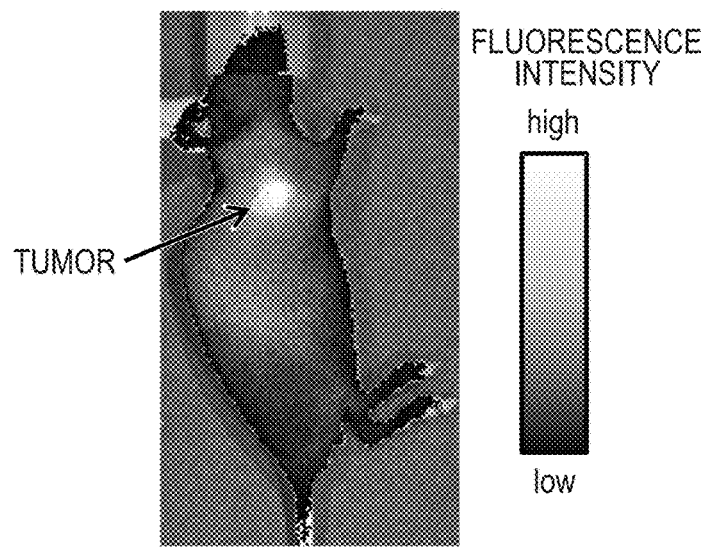
FIG. 1 illustrates a whole-body fluorescence image of a tumor-bearing mouse at hour 24 after administration of polymer PS4 of the present invention.

Preferred embodiments of the present invention will now be described in detail in accordance with the accompanying drawings.

Embodiment 1, Polymer (Polymer)

A polymer according to an embodiment of the present invention is described, but the present invention is not limited thereto. The polymer according to the present embodiment has a structure in which polysarcosine serves as a main chain and a near-infrared dye is conjugated to the polymer terminal. Specifically, the polymer has a structure represented by the following formula (P1).

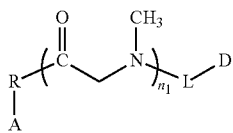

(P1)

In the formula (P1), R represents any of a residue derived from a polymerization initiator, or a functional group; A may not be present, and when present, A represents any of a low-molecular compound, a dye, a reporter molecule, a target-binding molecule, a polymer or D; L represents a linker and L may not be present; $n_1$ represents an integer of 1 or more; and D represents a dye backbone of a dye having absorption in the near-infrared region.

(Dye)

One example of D in the formula (P1) of the polymer according to the present embodiment can include one represented by the following formula (d1) or (d2).

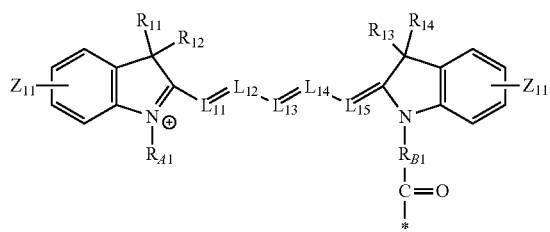

(d1)

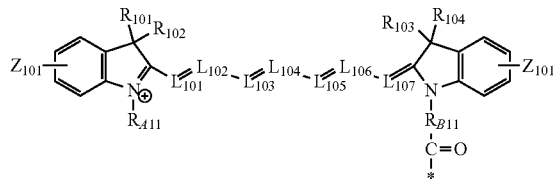

(d2)

In the formula (d1), $L_{11}$, $L_{12}$, $L_{13}$, $L_{14}$ and $L_{15}$ may be each the same or different, and represent CH or $CR_{15}$, and $R_{15}$ represents a straight or branched alkyl group having 1 to 10 carbon atoms. $L_{11}$, $L_{12}$, $L_{13}$, $L_{14}$ and $L_{15}$ may be taken together to form a 4-membered ring to a 6-membered ring. $R_{11}$, $R_{12}$, $R_{13}$ and $R_{14}$ may be each the same or different, and represent a hydrogen atom, a straight or branched alkyl group having 1 to 10 carbon atoms, $-R_{C1}-SO_3^-$, or $-R_{D1}-SO_3X_{11}$. $R_{C1}$ and $R_{D1}$ represent a straight or branched alkylene group having 1 to 10 carbon atoms. $X_{11}$ represents any of a hydrogen atom, a sodium atom, a potassium atom, or a cation derived from ammonia, triethylamine, lysine or arginine. $R_{A1}$ represents a straight or branched alkyl group having 1 to 10 carbon atoms, $-R_{E1}-SO_3^-$, $-R_{F1}-SO_3X_{12}$, or $-R_{G1}-CO_2X_{13}$. $X_{12}$ and $X_{13}$ represent any of a hydrogen atom, a sodium atom, a potassium atom, or a cation derived from ammonia, triethylamine, lysine or arginine. $R_{E1}$, $R_{F1}$ and $R_{G1}$ represent a straight or branched alkylene group having 1 to 10 carbon atoms. When $R_{A1}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion; $R_{B1}$ represents a straight or branched alkylene group having 1 to 10 carbon atoms; $Z_{11}$ represents a hydrogen atom or $-SO_3X_{14}$, or is taken together with an indole ring bound to $Z_{11}$ to form a cyclic aromatic ring including a benz[e]indole ring, a benz[f]indole ring or a benz[g]indole ring, and furthermore, a hydrogen atom in the cyclic aromatic ring may be substituted with a straight or branched alkyl group having 1 to 10 carbon atoms, a straight or branched alkoxy group having 1 to 10 carbon atoms, or $-SO_3X_{15}$. $X_{14}$ and $X_{15}$ represent any of a hydrogen atom, a sodium atom, a potassium atom, or a cation derived from ammonia, triethylamine, lysine or arginine, and * represents binding to L, or represents binding to the carbon atom at the terminal of the repeating unit in the formula (P1) when the polymer does not include L.

In the formula (d2), $L_{101}$, $L_{102}$, $L_{103}$, $L_{104}$, $L_{105}$, $L_{106}$ and $L_{107}$ may be each the same or different, and represent CH or $CR_{105}$, and $R_{105}$ represents a straight or branched alkyl group having 1 to 10 carbon atoms. $L_{101}$, $L_{102}$, $L_{103}$, $L_{104}$, $L_{105}$, $L_{106}$ and $L_{107}$ may be taken together to form a 4-membered ring to a 6-membered ring. $R_{101}$, $R_{102}$, $R_{103}$ and $R_{104}$ may be each the same or different, and represent a hydrogen atom, a straight or branched alkyl group having 1 to 10 carbon atoms, $-R_{C11}-SO_3^-$, or $-R_{D11}-SO_3X_{101}$. $R_{C11}$ and $R_{D11}$ represent a straight or branched alkylene group having 1 to 10 carbon atoms. $X_{101}$ represents any of a hydrogen atom, a sodium atom, a potassium atom, or a cation derived from ammonia, triethylamine, lysine or arginine. $R_{A11}$ represents a straight or branched alkyl group having 1 to 10 carbon atoms, $-R_{E11}-SO_3^-$, $-R_{F11}-SO_3X_{102}$, or $-R_{G11}-CO_2X_{103}$. $X_{102}$ and $X_{103}$ represent any of a hydrogen atom, a sodium atom, a potassium atom, or a cation derived from ammonia, triethylamine, lysine or arginine. $R_{E11}$, $R_{F11}$ and $R_{G11}$ represent a straight or branched alkylene group having 1 to 10 carbon atoms; when $R_{A11}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion; $R_{B11}$ represents a straight or branched alkylene group having 1 to 10 carbon atoms; $Z_{101}$ represents a hydrogen atom or —$SO_3X_{104}$, or is taken together with an indole ring bound to $Z_{101}$ to form a cyclic aromatic ring including a benz[e]indole ring, a benz[f]indole ring or a benz[g]indole ring, and furthermore, a hydrogen atom in the cyclic aromatic ring may be substituted with a straight or branched alkyl group having 1 to 10 carbon atoms, a straight or branched alkoxy group having 1 to 10 carbon atoms, or —$SO_3X_{105}$. $X_{104}$ and $X_{105}$ represent any of a hydrogen atom, a sodium atom, a potassium atom, or a cation derived from ammonia, triethylamine, lysine or arginine, and * represents binding to L, or represents binding to the carbon atom at the terminal of the repeating unit in the formula (P1) when the polymer does not include L.

Furthermore, examples of D can include the following (d3) and (d4).

or branched alkylene group having 1 to 10 carbon atoms. $X_{22}$ represents any of a hydrogen atom, a sodium atom, a potassium atom, or a cation derived from ammonia, triethylamine, lysine or arginine. $R_{A2}$ represents a straight or branched alkyl group having 1 to 10 carbon atoms, —$R_{E2}$—$SO_3^-$, —$R_{F2}$—$SO_3X_{23}$, or —$R_{G2}$—$CO_2X_{24}$. $X_{23}$ and $X_{24}$ represent any of a hydrogen atom, a sodium atom, a potassium atom, or a cation derived from ammonia, triethylamine, lysine or arginine. $R_{E2}$, $R_{F2}$ and $R_{G2}$ represent a straight or branched alkylene group having 1 to 10 carbon atoms. When $R_{A2}$ represents a straight or branched alkyl group having 1 to 10 carbon atoms, a halogen ion or an organic acid ion may be included as a counter ion. $R_{B2}$ represents a straight or branched alkylene group having 1 to 10 carbon atoms. * represents binding to L, or represents binding to the carbon atom at the terminal of the repeating unit in the formula (P1) when the polymer does not include L.

In the formula (d4), $R_{301}$ to $R_{312}$ may be each the same or different, and represent a hydrogen atom, a straight or branched alkyl group having 1 to 10 carbon atoms, or —$SO_3X_{31}$. $X_{31}$ represents any of a hydrogen atom, a sodium atom, a potassium atom, or a cation derived from ammonia, triethylamine, lysine or arginine. $L_{31}$, $L_{32}$, $L_{33}$, $L_{34}$, $L_{35}$, $L_{36}$

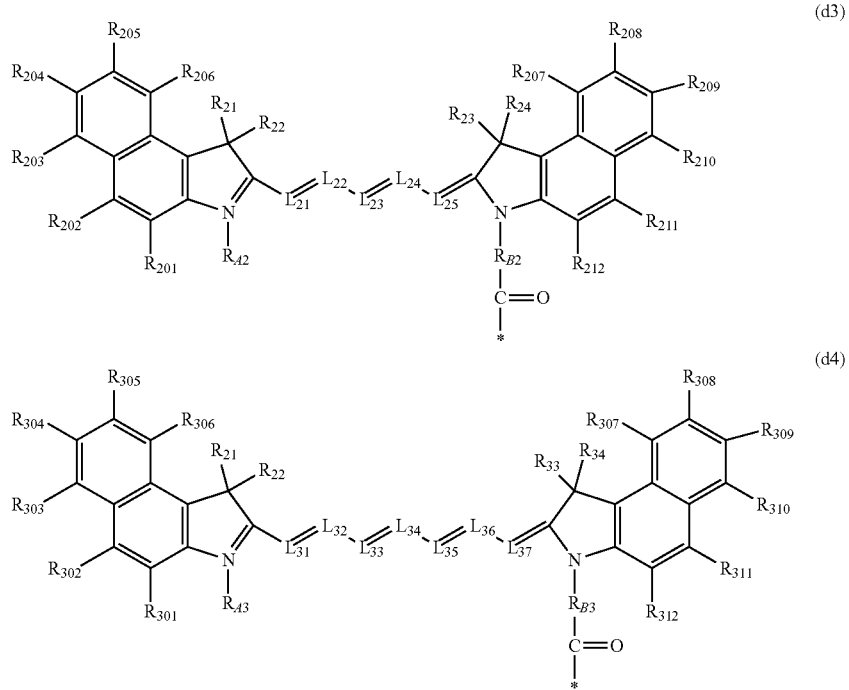

In the formula (d3), $R_{201}$ to $R_{212}$ may be each the same or different, and represent a hydrogen atom, a straight or branched alkyl group having 1 to 10 carbon atoms, or —$SO_3X_{21}$. $X_{21}$ represents any of a hydrogen atom, a sodium atom, a potassium atom, or a cation derived from ammonia, triethylamine, lysine or arginine. $L_{21}$, $L_{22}$, $L_{23}$, $L_{24}$ and $L_{25}$ may be each the same or different, and represent CH or $CR_{25}$, and $R_{25}$ represents a straight or branched alkyl group having 1 to 10 carbon atoms. $L_{21}$, $L_{22}$, $L_{23}$, $L_{24}$ and $L_{25}$ may be taken together to form a 4-membered ring to a 6-membered ring. $R_{21}$, $R_{22}$, $R_{23}$ and $R_{24}$ may be each the same or different, and represent a hydrogen atom, a straight or branched alkyl group having 1 to 10 carbon atoms, —$R_{C2}$—$SO_3^-$, or —$R_{D2}$—$SO_3X_{22}$. $R_{C2}$ and $R_{D2}$ represent a straight and $L_{37}$ may be each the same or different, and represent CH or $CR_{35}$, and $R_{35}$ represents a straight or branched alkyl group having 1 to 10 carbon atoms. $L_{31}$, $L_{32}$, $L_{33}$, $L_{34}$, $L_{35}$, $L_{36}$ and $L_{37}$ may be taken together to form a 4-membered ring to a 6-membered ring. $R_{31}$, $R_{32}$, $R_{33}$ and $R_{34}$ may be each the same or different, and represent a hydrogen atom, a straight or branched alkyl group having 1 to 10 carbon atoms, —$R_{C3}$—$SO_3^-$, or —$R_{D3}$—$SO_3X_{32}$. $R_{C3}$ and $R_{D3}$ represent a straight or branched alkylene group having 1 to 10 carbon atoms. $X_{32}$ represents any of a hydrogen atom, a sodium atom, a potassium atom, or a cation derived from ammonia, triethylamine, lysine or arginine. $R_{A3}$ represents a straight or branched alkyl group having 1 to 10 carbon atoms, —$R_{E3}$—$SO_3^-$, —$R_{F3}$—$SO_3X_{33}$, or —$R_{G3}$—

$CO_2X_{34}$. $X_{33}$ and $X_{34}$ represent any of a hydrogen atom, a sodium atom, a potassium atom, or a cation derived from ammonia, triethylamine, lysine or arginine. $R_{E3}$, $R_{F3}$ and $R_{G3}$ represent a straight or branched alkylene group having 1 to 10 carbon atoms. When $R_{A3}$ represents a straight or branched alkyl group having 1 to 10 carbon atoms, a halogen ion or an organic acid ion may be included as a counter ion. $R_{B3}$ represents a straight or branched alkylene group having 1 to 10 carbon atoms. * represents binding to L, or represents binding to the carbon atom at the terminal of the repeating unit in the formula (P1) when the polymer does not include L.

R represents any of a residue derived from a polymerization initiator, or a functional group, as described above. The functional group here includes, in addition to all general functional groups, groups derived from a low-molecular compound, a dye, a reporter molecule, a target-binding molecule, a polymer and the like represented by A in the formula (P1). The groups derived from a low-molecular compound, a dye, a reporter molecule, a target-binding molecule, a polymer and the like represented by A represent such groups that are each bound via the residue derived from a polymerization initiator.

The functional group as R in the polymer according to the present embodiment includes any groups, and one example thereof can include an alkyl group, a hydroxyl group, a carboxyl group, an amino group, a thiol group, an azido group, a diamine, a succinimidyl ester group, a maleimide group and a succinimide group. Examples of the low-molecular compound as A include an inhibitor such as gefitinib. Examples of the reporter molecule as A include a molecule generating a physical signal such as a radioactive signal, a magnetic field signal, an ultrasonic signal, a fluorescent signal or an optical ultrasonic signal, and radioactive halogen, radioisotope, a paramagnetic metal ion, an iron oxide particle, a gold nanoparticle, a microbubble, a dye and an anticancer agent that are therapeutic agents. Examples of the dye as A include a fluorescent compound, a phosphorescent compound and a near-infrared light absorbing compound. Examples of the target-binding molecule as A include an antibody, an antibody fragment and artificial antibodies such as a single-strand antibody, and an enzyme, bioactive peptide, glycopeptide, a sugar chain, a lipid and a molecule-recognizing compound. Examples of other polymer as A include polyethylene glycol, and such a polymer may have any degree of polymerization and may also be ethylene glycol.

When L is present, one example of L includes structures including the following formulas (l1) to (l13), or a structure including polyethylene glycol. In the following formulas (l1) to (l13), * represents binding to other atoms. The following formulas (l1) to (l13) may be used singly, or the same type of formula or a plurality of formulas may be repeatedly used.

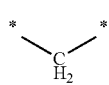

(l1)

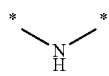

(l2)

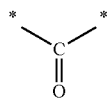

(l3)

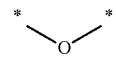

(l4)

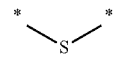

(l5)

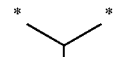

(l6)

(l7)

(l8)

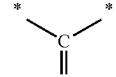

(l9)

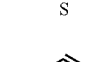

(l10)

(l11)

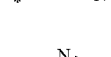

(l12)

(l13)

In the above chemical structures, * represents direct binding or indirect binding to D above or the carbon atom at the terminal of the repeating unit.

Formation of L above can be conducted by using, for D above, one having a reactive group such as an amino group, a hydroxyl group, a thiol group, a carboxyl group, an epoxy group, a glycidyl group, an N-succinimidyloxy group, an N-sulfosuccinimidyl group, an N-maleimide alkyl group, an iodoacetamide group, a bromoacetamide group, an isothiocyano group, a sulfonic acid chloride group and a carboxylic acid chloride group, to generate a bond between the reactive groups selected as a combination that allows a binding reaction to occur. When the bond generated above includes a Schiff base and a carbonyl group, such base and carbonyl group can be subjected to reduction to achieve further stabilization of the bond.

Examples of the formula (P1) include a polymer represented by the following formula (1), (2) or (3). In the polymer represented by the formula (2), a reporter molecule or a target-binding molecule can further be introduced directly to a phenylmethylene group at the terminal, or after a benzyloxycarbonyl group is subjected to deprotection. $n_{11}$, $n_{12}$ and $n_{13}$ represent an integer of 1 or more.

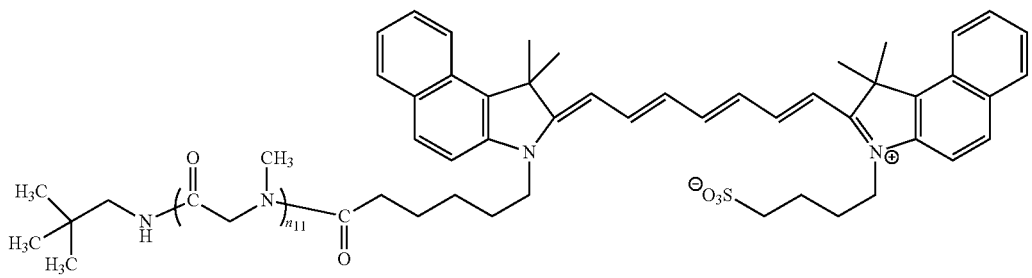

(1)

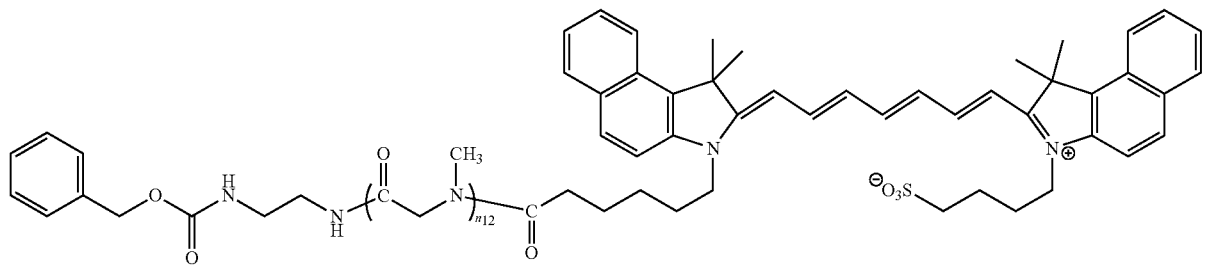

(2)

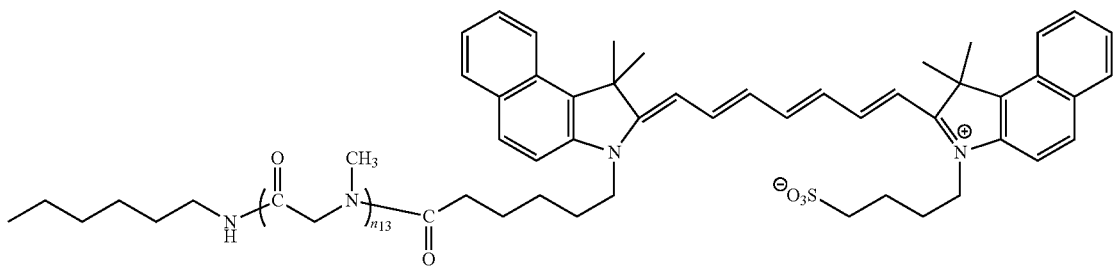

(3)

(Reason for Increase in Tumor/Blood Ratio)

One mechanism that is considered as a reason for an increase in the tumor/blood ratio of the polymer according to the present embodiment is described. An example is here described where polysarcosine (hereinafter, sometimes abbreviated as "PSAR") serves as the main chain in the formula (P1) and ICG is included as the near-infrared dye represented by D. An increase in the sarcosine concentration in a tumor site of prostate cancer or the like has been heretofore reported NPL 1. Not only such a mechanism, but also the Enhanced Permeability and Retention (hereinafter, sometimes abbreviated as "EPR") effect where a blood vessel is less in the vicinity of a tumor is considered to allow ICG-conjugated PSAR present in blood to be accumulated in the tumor. PSAR is a polymer in which a sarcosine monomer is bound by an amide bond, the binding mode is the same as in polypeptide, and therefore PSAR is considered to be subjected to enzymatic degradation in a living body as in polypeptide. The sarcosine monomer has been reported to be metabolized and converted to glycine by sarcosine dehydrogenase (NPL 1). Therefore, a probe retained in blood is metabolized and excreted by degradation with the lapse of time, and it is thus considered that the concentration in blood is reduced. As a result, the effect of increasing the tumor/blood ratio is exerted. On the other hand, ICG-conjugated PEG in the prior art is not degraded but retained in blood for a long period, and thus the tumor/blood ratio is low. The sarcosine is represented by the formula (s1), and is hereinafter sometimes abbreviated as "SAR".

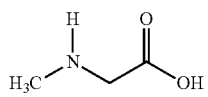

(s1)

(Contrast Agent for Photoacoustic Imaging)

The contrast agent for photoacoustic imaging according to the present invention includes the polymer singly or includes the polymer and a dispersion medium. Examples of the dispersion medium include saline, distilled water for injection, phosphate buffered saline and an aqueous glucose solution. The contrast agent for photoacoustic imaging according to the present invention may also include if necessary a pharmacologically acceptable additive, for example, a vasodilator. The contrast agent for photoacoustic imaging according to the present invention may be dispersed in the dispersion medium in advance, or may be in the form of a kit and be dispersed in the dispersion medium for use before administration into a living body. The contrast agent for photoacoustic imaging according to the present invention can utilize the EPR effect to thereby be more accumulated in a tumor site than a normal site in a living body in administration thereof into the living body. Furthermore, the concentration in blood is rapidly reduced and therefore the effect of increasing the tumor/blood ratio is exerted. As a result, when the contrast agent is administered into a living body and thereafter the living body is irradiated with light for detection of an acoustic wave, a larger signal can be detected from a tumor site than a normal site. As described above, the contrast agent for photoacoustic imaging according to the present invention can be suitably used for imaging a tumor.

Furthermore, the contrast agent for photoacoustic imaging according to the present invention can also be used for an application where a cellular uptake mechanism is utilized to image an associated disease. For example, the polymer of the present invention is supposed to be taken up in cells by macropinocytosis as described in Examples, and therefore such a mechanism can be expected to be useful in an application where an increased disease part is selectively imaged.

(Method for Producing Polymer)

The method for producing the polymer according to the present embodiment includes the following two steps of:
(1) polymerizing sarcosine NCA (α-amino acid-N-carboxylic anhydride) represented by the formula (s2) as a monomer by use of a polymerization initiator to provide polysarcosine, and
(2) binding the polysarcosine obtained by polymerization in step (1) to a near-infrared dye.
The method can also include, in addition to steps (1) and (2), the following step of:
(3) purifying the near-infrared dye-conjugated polysarcosine obtained in step (2) to result in an increase in purity.

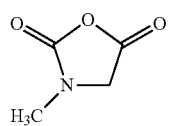

(s2)

(Step (1))
(Sarcosine, Polysarcosine)

In the present embodiment, SAR is also designated as "N-methyl-glycine". PSAR as the main chain in the present embodiment is a water-soluble polymer, and has the properties of a high biocompatibility and low cytotoxicity. PSAR is also expected to be degraded and metabolized in a living body. The molecular weight and the average molecular weight described later represent the weight average molecular weight, unless particularly indicated.

The average molecular weight of PSAR as the polymer of the present embodiment is preferably 6000 or more, further preferably 13000 or more. The upper limit of the average molecular weight is preferably in the range of 100000 or less, further preferably 50000 or less. That is, the average molecular weight of the polymer is preferably 6000 or more and 100000 or less, further preferably 6000 or more and 50000 or less, further preferably 13000 or more and 50000 or less.

When the average molecular weight is 6000 or more, the EPR effect can allow the polymer to be more accumulated in a tumor site than a normal site in a living body. The molecular weight of the polymer can be 50000 or less because progress of a polymerization reaction is more difficult and the solution viscosity is increased according to an increase in the molecular weight of the polymer. The polymer according to the present embodiment, including PSAR having such properties and the dye, and a contrast agent for photoacoustic imaging, including the polymer, are each accumulated in a tumor site and have a rapidly reduced concentration in blood, and therefore exert the effect of increasing the tumor/blood ratio.

In the present embodiment, the molecular weight of the polymer can be measured by the GPC method or the proton NMR method.

SAR is polymerized in the same manner as in the polymerization reaction of an α-amino acid to produce PSAR. While the polymerization reaction can be performed by using any method, a method by use of α-amino acid-N-carboxylic anhydride (NCA) can be adopted because of providing a polymer high in the degree of polymerization. Examples of the method of producing NCA of SAR can include a reaction of SAR and phosgene in an organic solvent such as dioxane or tetrahydrofuran, and a reaction of SAR (N-α-Carbobenzoxysarcosine) protected with a carbobenzoxy group (also referred to as "benzyloxycarbonyl group") and thionyl chloride.

(Polymerization Initiator)

Any substance can be used as the polymerization initiator, and amine and alkoxide (in particular, organometallic alkoxide) can be adopted as a polymerization initiator that allows the reaction to efficiently progress at a room temperature. The polymerization can be performed based on a common reaction, and a side-reaction due to degradation by warming of NCA and/or incorporation of water can be suppressed. Examples include a method including sufficiently removing water in a glove box filled with an inert gas (nitrogen gas) and performing stirring by use of a Schlenk tube filled with an inert gas at room temperature for a long period. The inert gas can be allowed to continuously flow upon the polymerization reaction, thereby removing carbon dioxide generated in the reaction, to provide a polymer. The degree of PSAR can be adjusted by the ratio of the molar number of NCA of SAR to the molar number of the polymerization initiator. In order to provide PSAR having a high molecular weight by polymerization, a polymerization initiator selected from the following formula (i1) or (i2) can be adopted in terms of high industrial convenience and purity.

(i1)

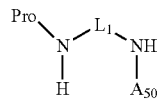

(i2)

In the formula (i1), $R_{41}$ represents a straight or branched alkyl group having 5 or less carbon atoms, and $A_{40}$ represents a hydrogen atom or $R_{41}$. In the formula (i2), $L_1$ represents a straight alkylene group having 3 or less carbon atoms, Pro represents a benzyloxycarbonyl (hereinafter, sometimes abbreviated as "Cbz" or "Z") group, a tert-butoxycarbonyl (hereinafter, sometimes abbreviated as "Boc") group, a p-toluenesulfonyl (hereinafter, sometimes abbreviated as "tosyl", "Tos" or "Ts") group and a 2-nitrobenzenesulfonyl (hereinafter, sometimes abbreviated as "nosyl" or "Ns") group, and $A_{50}$ represents a hydrogen atom, or a straight or branched alkyl group having 5 or less carbon atoms. Pro represents a protective group, and can be subjected to deprotection after the polymerization reaction or can be further bound to a reporter molecule or a target-binding molecule via the protective group, or the protective group can be substituted with a reporter molecule or a target-binding molecule.

PSAR as the main chain of the polymer according to the present embodiment can be functionalized by introduction of a functional group by any of various methods described below. Examples of a functional group that can be introduced at the α-position, derived from the polymerization initiator, include an alkenyl group, an alkyl group, an amino group, an aldehyde group and a thiol group. Alkyne can be subjected to azide-alkyne cyclic addition by a click reaction. A compound having a thiol group can be added to alkyne by a thiol-ene click reaction. As another example, any functional group can be used as long as the group can react with secondary amine that is at the w-position of PSAR in completion of the polymerization reaction.

(Step (2))

Specifically, with respect to the polymer according to the present embodiment and the contrast agent for photoacoustic imaging, including the polymer, a dye having a succinimidyl ester group is reacted with secondary amine of PSAR, to thereby allow the dye to be covalently bound, but the introduction method of the dye is not limited thereto. The above reaction can allow a reporter molecule or a target-binding molecule to be introduced to PSAR as the main chain of the polymer. The reporter molecule here means a molecule or a therapeutic agent that generates a physical signal such as a radioactive signal, a magnetic field signal, an ultrasonic signal, a fluorescent signal or an optical ultrasonic signal, and examples include radioactive halogen, radioisotope, a paramagnetic metal ion, an iron oxide particle, a gold nanoparticle, a microbubble, a dye and an anticancer agent. While examples of the dye include a fluorescent compound and a phosphorescent compound, a molecule that generates an optical ultrasonic signal may have the property of absorbing light in the wavelength region depending on the object. The polymer can have the reporter molecule to thereby be utilized as a contrast agent for an enhancement in contrast. The target-binding molecule here means a substance that is selectively bound to a target specific to a tumor and the periphery thereof, and can be arbitrarily selected from compounds such as a biomolecule and a pharmaceutical product. Specific examples include an antibody, an antibody fragment and artificial antibodies such as a single-strand antibody, and an enzyme, bioactive peptide, glycopeptide, a sugar chain, a lipid and a molecule-recognizing compound. Such substances can be used singly or in combinations of a plurality thereof. A compound to which the target-binding molecule is bound can be used to thereby allow a target specific to a tumor and the periphery thereof to be detected, to monitor dynamics, localization, drug efficacy, metabolism and the like.

(Near-Infrared Dye)

The dye for use in the present embodiment is a molecule that generates a physical signal such as a fluorescent signal or an optical ultrasonic signal. The polymer according to the present embodiment can have one or more dyes to thereby be used as a diagnostic contrast agent, most preferably as a contrast agent for photoacoustic imaging. As the dye, a dye can be adopted which has the property of absorbing light in the near-infrared wavelength region, the light being relatively high in permeability into a human body. Examples of the dye for use in the present embodiment include a fluorescent dye, and a dye low in fluorescence quantum yield can be adopted because the energy absorbed is more used in a photoacoustic signal than fluorescence. Furthermore, when a fluorescent dye has the property of light absorption even in the extinction state, the dye can obtain a photoacoustic signal. The near-infrared wavelength region here is in the range from 600 nm to 1300 nm. Examples of the near-infrared organic dye in the present embodiment can include an azine type dye, an acridine type dye, a triphenylmethane type dye, a xanthene type dye, a porphyrin type dye, a cyanine type dye, a phthalocyanine type dye, a styryl type dye, a pyrylium type dye, an azo type dye, a quinone type dye, a tetracycline type dye, a flavone type dye, a polyene type dye, a BODIPY (registered trademark) type dye and an indigoid type dye. Other examples can include indocyanine green (ICG), ICG-sulfo-OSu (registered trademark), ICG-EG$_4$-sulfo-OSu (registered trademark), ICG-EG$_8$-sulfo-OSu (registered trademark) (produced by Dojindo), Alexa Fluor (registered trademark) type dyes (produced by Life Technologies Japan) such as Alexa Fluor (registered trademark) 750, a Cy (registered trademark) type dye (produced by GE Healthcare), IR-783, IR-806 and IR-820 (produced by Sigma Aldrich Japan), IR Dye 700DX (registered trademark), IR Dye 800CW (registered trademark) and IR Dye 800RS (registered trademark) (produced by LI-COR), ADS780WS, ADS795WS, ADS830WS and ADS832WS (produced by American Dye Source), a DyLight (registered trademark) type dye (produced by Thermo Fisher Scientific), a Hilyte Fluor (registered trademark) type dye (produced by AnaSpec Inc.), and a DY (registered trademark) type dye (produced by Dyomics GmbH). A dye having a succinimidyl ester group can be adopted because being capable of being reacted with PSAR to form a covalent bond. A functional group like a succinimidyl ester group can also be introduced to a generally commercially available dye and bound to PSAR. The dye can be conjugated to PSAR by any of a non-covalent bond and a covalent bond, or a combination thereof. In the case of administration into a body, it is desirable that the dye and PSAR as the main chain be integrated for a certain time or more, and therefore it is desirable that the dye and PSAR be bound by a covalent bond in the polymer.

Examples of the dye for use in the present embodiment include the following formulas (d1-1) to (d1-10).

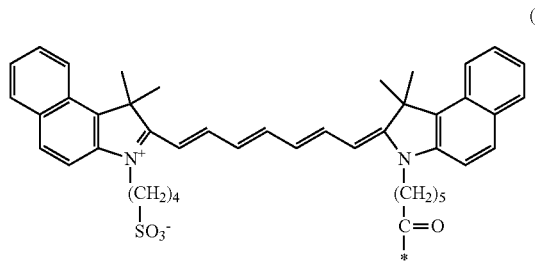

(d1-1)

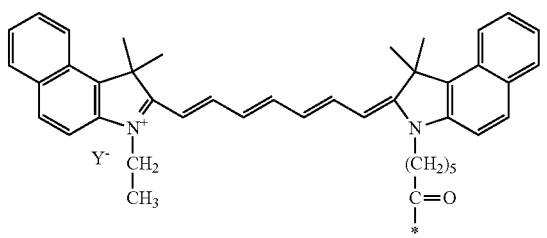

(d1-2)

-continued
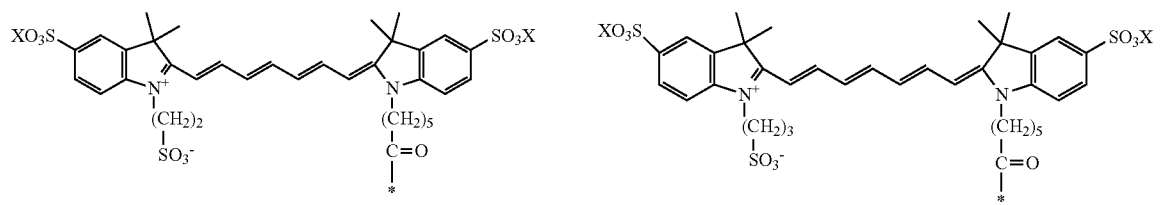
(d1-3)
(d1-4)
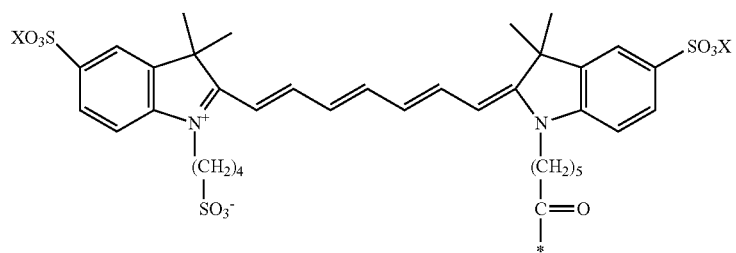
(d1-5)
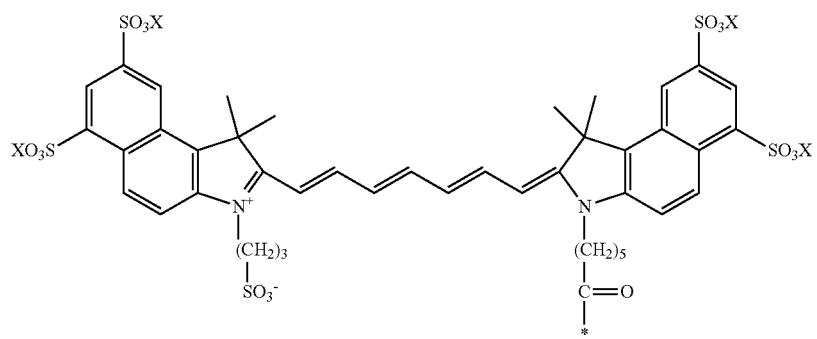
(d1-6)
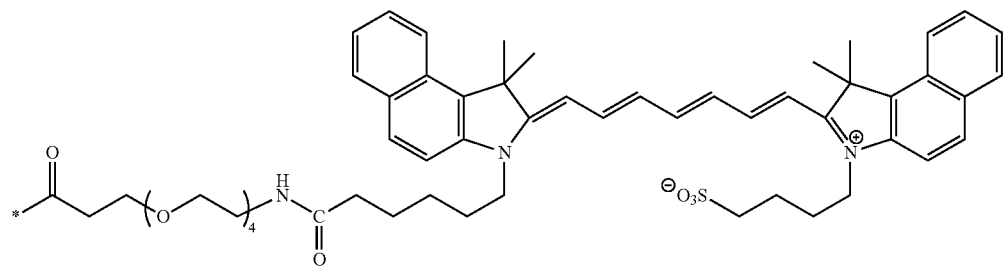
(d1-7)
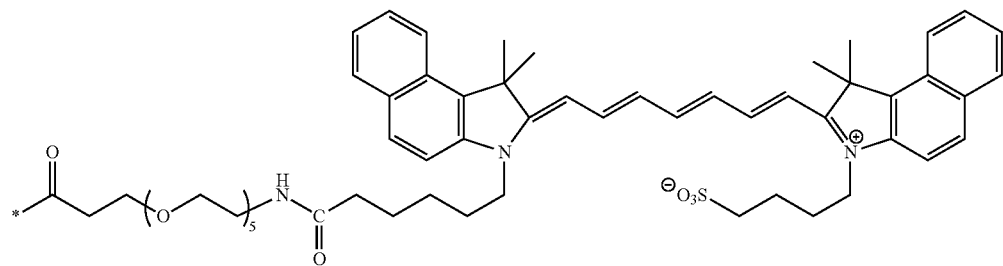
(d1-8)

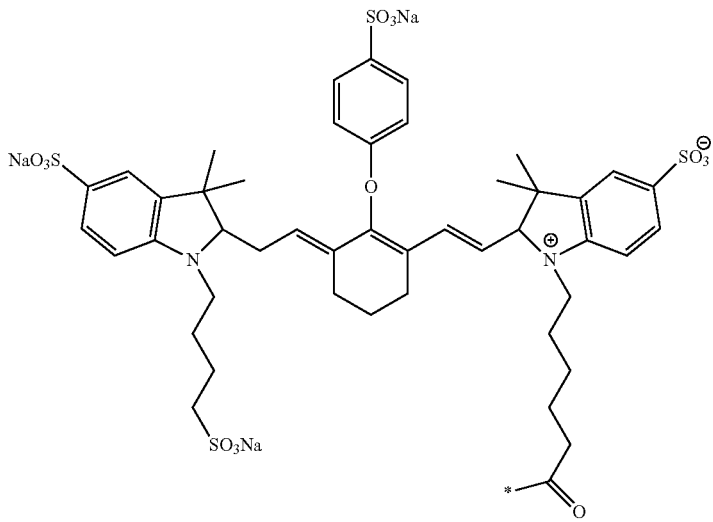

(d1-9)

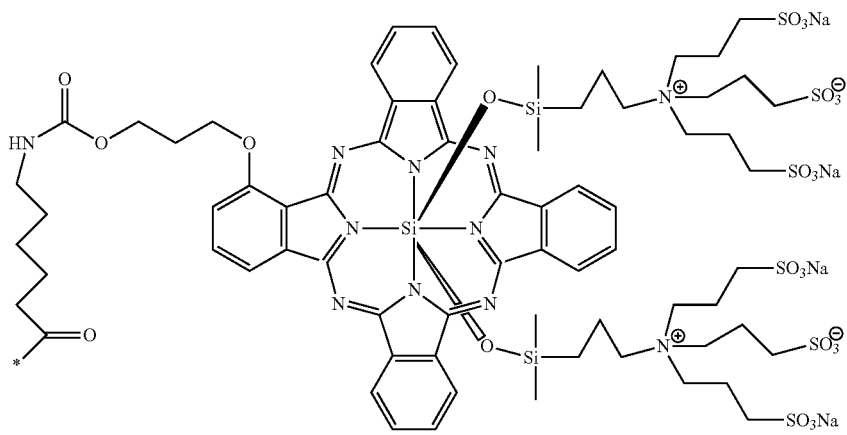

(d1-10)

In the formulas (d1-1) to (d1-10), * represents binding to L in the formula (P1) or the formula (1), or represents direct binding to a carbon atom at a terminal of a repeating unit in the formula (P1) or the formula (1) when the polymer does not include L.

(Step (3))

The method of purifying the polymer according to the present embodiment includes chromatography (including High Pressure Liquid Chromatography) using various columns, a dialysis purification method, and a recrystallization method, but not limited thereto. Particularly, when ICG is conjugated to the polymer according to the present embodiment, a dialysis purification method in which is methanol is used for a dialysis outer liquid is effective for removal of the unreacted ICG. The reason can be described as follows. ICG interacts with a chromatography carrier particularly in an aqueous solvent, and the ICG bound to the polymer has difficulty in being separated from the unreacted ICG. ICG also non-specifically interacts with the polymer in an aqueous solvent in a dialysis method, and such separation is difficult to perform. On the other hand, the unreacted ICG can be free from the polymer and diffused in the dialysis outer liquid in the dialysis method using methanol, to provide a polymer having a high purity.

(Photoacoustic Imaging Method)

The method for detecting the contrast agent for photoacoustic imaging according to the present invention, administered into a living body, by use of a photoacoustic imaging apparatus is described. Herein, the photoacoustic imaging is a concept including photoacoustic tomography (tomographic method). The method for detecting the contrast agent for photoacoustic imaging according to the present invention includes the following steps (a) and (b). Herein, the photoacoustic imaging method according to the present invention may include other step(s) than the steps shown below:

(a) a step of irradiating a specimen, to which the contrast agent for photoacoustic imaging according to the present invention is administered, with light in a wavelength region from 600 nm to 1300 nm, and (b) a step of detecting an acoustic wave emitted from the contrast agent for photoacoustic imaging present in the specimen.

The method for detecting the contrast agent for photoacoustic imaging according to the present invention may include a step of reconstructing a spatial photoacoustic signal intensity distribution from the wavelength, phase, time information and the like of the acoustic wave obtained in step (b) above. Herein, three-dimensional image reconstruction can be conducted based on the wavelength, phase and time information of the photoacoustic signal obtained in step (b) above. Data obtained by the image reconstruction may take any form as long as the position information of the intensity distribution of the photoacoustic signal can be grasped from the data. For example, a form may be taken in which the photoacoustic signal intensity is exhibited on a three-dimensional space, or a form may be taken in which the photoacoustic signal intensity is exhibited on a two-dimensional plane. In addition, the following form can also be taken: information on the same observation object is acquired by a different imaging method and the positional correspondence relationship between such pieces of information and the photoacoustic intensity distribution is acquired. In step (a) above, the specimen to which the polymer according to the present embodiment is administered by a method such as oral administration or injection can be used. In step (b) above, an apparatus that emits light with which the specimen is irradiated, and an apparatus that detects the photoacoustic signal emitted from the polymer according to the present embodiment are not particularly limited. A light source for irradiation of the specimen with light in step (b) above is not limited as long as the light source can irradiate the specimen with laser pulse light having at least one wavelength selected from the range from 600 nm to 1300 nm. Examples of the apparatus for irradiating the specimen with laser pulse light include a titanium sapphire laser (LT-2211-PC, manufactured by Lotis TII), an OPO laser (LT-2214 OPO, manufactured by Lotis TII) and an alexandrite laser. The apparatus for detecting the acoustic wave is not particularly restricted and various apparatuses can be used. For example, such detection can be conducted using a commercially available photoacoustic imaging apparatus (Nexus128, manufactured by Endra Inc.).

The imaging method using the contrast agent for photoacoustic imaging according to the present invention can image an objective site such as a tumor or a blood vessel through steps (a) and (b) above.

Embodiment 2

A further embodiment of the present invention can include the following polymer.

A polymer represented by the following formula (P2), having a molecular weight of 8000 or more:

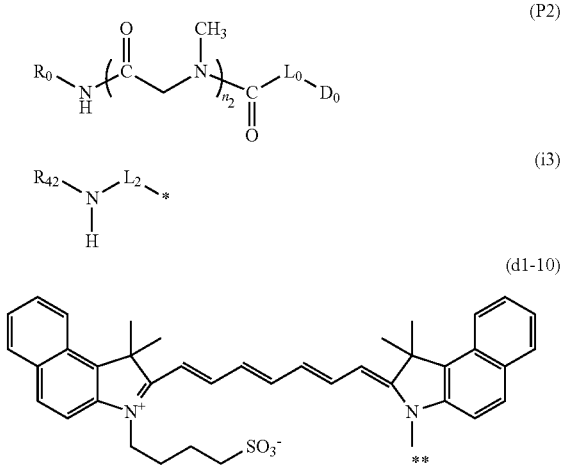

wherein in the formula (P2), $n_2$ represents an integer of 1 or more; $R_0$ represents a straight or branched alkyl group having 1 to 5 carbon atoms, or a group represented by the formula (i3); $L_0$ represents an alkylene group or an oxyalkylene group having 1 to 10 carbon atoms, or may not be present; and $D_0$ represents the formula (d1-10);

$L_2$ represents a straight alkylene group having 1 to 3 carbon atoms; $R_{42}$ represents any of a Z group, a Boc group, a tosyl group and a nosyl group; * in the formula (i3) represents binding to a nitrogen atom in the formula (P2); and ** in the formula (d1-10) represents binding to $L_0$ or represents binding to a carbon atom at a terminal of a repeating unit in the formula (P2) when $L_0$ in the formula (P2) is not present.

$R_0$ can be represented by the following formula (i4) or (i5):

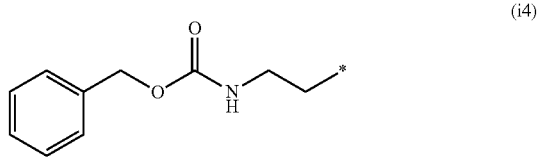

wherein * in each of the formulas (i4) and (i5) represents binding to a nitrogen atom in the formula (P2).

The present embodiment further includes a method for producing a polymer, the method including a step of performing a polymerization reaction of sarcosine NCA as a monomer with a polymerization initiator represented by the following formula (i6) or (i7), to provide a polymer, and a step of binding the polymer obtained in the step to a compound represented by the following formula (d1-11):

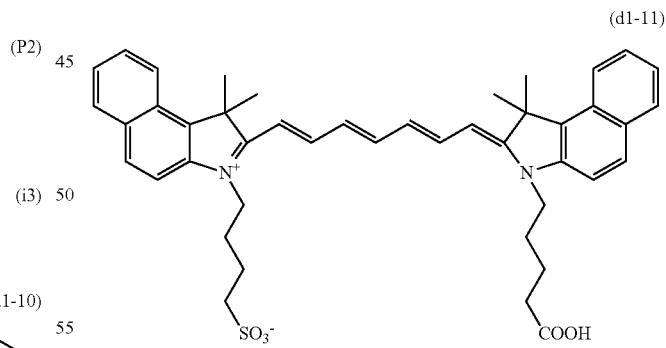

wherein in the formula (i6), $R_{43}$ represents a straight or branched alkylene group having 1 to 5 carbon atoms; and in the formula (i7), $R_{44}$ represents any of a Z group, a Boc group, a tosyl group and a nosyl group.

Embodiment 3

A further embodiment of the present invention can include a polymer represented by the following formula (P3), having a molecular weight of 8000 or more:

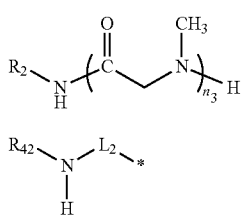

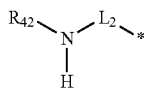

wherein in the formula (P3), $n_3$ represents an integer of 1 or more; $R_2$ represents a straight or branched alkyl group having 1 to 5 carbon atoms, or a group represented by the formula (i3); * in the formula (i3) represents binding to a nitrogen atom in the formula (P3); $L_2$ represents a straight alkylene group having 1 to 3 carbon atoms; and $R_{42}$ represents any of a Z group, a Boc group, a tosyl group and a nosyl group.

The present embodiment includes a method for producing a polymer, the method including a step of performing a polymerization reaction of sarcosine NCA as a monomer with a polymerization initiator represented by the following formula (i1) or (i2):

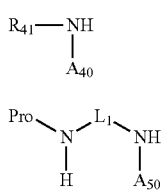

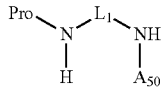

wherein in the formula (i1), $R_{41}$ represents a straight or branched alkyl group having 5 or less carbon atoms; and $A_{40}$ represents a hydrogen atom or $R_{41}$; and in the formula (i2), $L_1$ represents a straight alkylene group having 3 or less carbon atoms, Pro represents any of a Z group, a Boc group, a tosyl group and a nosyl group, and $A_{50}$ represents a hydrogen atom, or a straight or branched alkyl group having 5 or less carbon atoms.

EXAMPLES

Hereinafter, the present invention is described with reference to Examples in more detail, but the present invention is not limited to such Examples.

Example 1

(Synthesis of Dye-Conjugated PSAR)

N-α-Carbobenzoxysarcosine (produced by Kokusan Chemical Co., Ltd., 5 g) and thionyl chloride (produced by Wako Pure Chemical Industries, Ltd., 5 mL) were mixed, and warmed in an oil bath warmed to 55° C. for 5 to 10 minutes. The solution after the reaction was dropped to petroleum ether (produced by Nacalai tesque, Inc., 100 ml) to precipitate an insoluble substance, and well admixed and thereafter filtered by use of a glass filter to recover a precipitate. The precipitate was sufficiently dried in vacuum, and thereafter was dissolved in super-dehydrated ethyl acetate (produced by Wako Pure Chemical Industries, Ltd., 20 ml). The insoluble substance was removed by the glass filter, and the resultant was dropped in petroleum ether (50 ml) to precipitate an insoluble substance, and well admixed. Thereafter, the glass filter was used for filtration to recover a precipitate, the precipitate was dried in vacuum and thereafter subjected repeatedly twice to a series of operations of dissolution in super-dehydrated ethyl acetate, removal by the filter, and addition of petroleum ether. The above operations allowed NCA of SAR to be recovered. ($^1$H NMR (400 MHz, $CDCl_3$): δ (ppm)=4.13 (2H, s, —$CH_2$—CO—), 3.05 (3H, S, —$CH_3$))

Hexylamine (hereinafter, abbreviated as "HEA", produced by Wako Pure Chemical Industries, Ltd.), N-carbobenzoxy-1,2-diaminoethane (hereinafter, abbreviated as "Z-EDA", produced by Tokyo Chemical Industry Co., Ltd.), or neopentylamine (hereinafter, abbreviated as "NPA", produced by Tokyo Chemical Industry Co., Ltd.) was used for the polymerization initiator in the polymerization reaction, and super-dehydrated dimethylformamide (hereinafter, sometimes abbreviated as "DMF", produced by Wako Pure Chemical Industries, Ltd.) was used as a reaction solvent. The polymerization reaction was performed at room temperature by admixing in a Schlenk tube from which water was sufficiently removed and which was purged with a nitrogen gas. Table 1 shows the type of the polymerization initiator, the mixing ratio of the monomer to the polymerization initiator on a molar number basis at the initiation of the reaction, and the polymerization reaction time, in the polymerization reaction. The solution after the reaction was dissolved in ice cooled diethyl ether (produced by Wako Pure Chemical Industries, Ltd., 20 ml), and PSAR precipitated was recovered by centrifugation (2000 rpm, 4° C., 15 minutes). PSAR (100 mg) recovered was dissolved in 50 mM borate buffer (pH 8.5, 1 ml), ICG-Sulfo-OSu (produced by Dojindo, 1 mg/100 µl dimethyl sulfoxide (hereinafter, sometimes abbreviated as "DMSO", produced by Wako Pure Chemical Industries, Ltd.)) was added thereto, and the reaction was performed under light shielding at room temperature for 24 hours. The solution after the reaction was dialyzed to methanol (produced by Kishida Chemical Co., Ltd.) using Spectra/Por (registered trademark) 7 Dialysis Membrane (manufactured by Spectrum Laboratories, Inc.), for purification. Binding of PSAR and ICG was confirmed by electrophoresis. Prepared Polymers (ICG-conjugated PSAR) are called PS1, PS2, PS3 and PS4 as summarized in Table 1, hereinafter. PS1 obtained in the above method is represented by the formula (3), and $n_{13}$ represents an integer so that the average molecular weight of the PSAR portion is 3800. Similarly, PS2 and PS3 are represented by the formula (2), and each $n_{12}$ represents an integer so that the average molecular weights of the PSAR portion is 6000 (PS2) or 8000 (PS3). Similarly, PS4 is represented by the formula (1), and $n_{11}$ represents an integer so that the average molecular weight of the PSAR portion is 26000.

TABLE 1

| Polymer | Type of polymerization initiator | Monomer/polymerization initiator mixing ratio | Reaction time (hours) | Average molecular weight of PSAR portion |
|---|---|---|---|---|
| PS1 | HEA | 90 | 24 | 3800 |
| PS2 | Z-EDA | 200 | 24 | 6000 |
| PS3 | Z-EDA | 200 | 48 | 8000 |
| PS4 | NPA | 400 | 110 | 26000 |

Example 2

(Molecular Weight Evaluation)

The molecular weight of PSAR before binding of ICG, of each of polymers PS1 to PS4 prepared, was evaluated by a Gel Permeation Chromatography (hereinafter, sometimes abbreviated as "GPC") system (manufactured by Shimadzu Corporation). Specifically, a GPC system was used which was configured from CBM-20A as a system controller, LC-20AD as a liquid-feeding unit for analysis, DGU-20A3 as an online degasser, CTO-20AC as a column oven, RID-10A as a differential refractive index detector, SPD-20A as a UV-VIS detector, and an LC work station and GPC software. PLgel MIXED-E (manufactured by Agilent Technologies) was used as a column for analysis, and DMF was used as an eluent. Polyethylene glycol (hereinafter, sometimes abbreviated as "PEG") was used as a standard molecular weight substance for performing calibration. A solution of PSAR in DMF was allowed to flow into the column set at a flow rate of 0.5 ml/min at 40° C., and the molecular weight was calculated from the elution time (Table 1). The average molecular weight was increased according to increases in the ratio of the monomer loaded and the reaction time. When NPA was used as the polymerization initiator, the molecular weight tended to be most increased.

Example 3

(Evaluation of Tumor Accumulation Property and Evaluation of Concentration in Blood)

The amount of the polymer accumulated to a tumor was evaluated using a tumor bearing mouse in Examples of the present invention. For the mouse, a female outbred BALB/c slc-nu/nu mouse (6-week-old at the time of purchase) (Japan SLC, Inc.) was used. For one week before inoculation of tumor cells to the mouse, the animals were housed with normal diet and chips and allowed free access to food and water. Mouse rectum cancer cell lines (colon 26) ($10^6$ cells) were subcutaneously implanted to the mouse, and the mouse was raised until the size of the tumor reached 5 to 10 mm. The polymer of the present invention (13 nmol as the amount of the dye) was administered to the tumor bearing mouse, and fluorescence imaging of the tumor bearing mouse at 24 hours after administration was performed. The fluorescence imaging was performed using IVIS (registered trademark) Imaging System (manufactured by XENOGEN). FIG. 1 illustrates the fluorescence image of the tumor bearing mouse at 24 hours after administration of polymer PS4 of the present invention. Strong fluorescence was observed from polymer PS4 accumulated in the tumor.

In order to confirm the tumor accumulation property of the polymer of the present invention, the mouse was euthanized by a carbon dioxide gas at 10 or 24 hours after polymer administration, and a tumor tissue was resected. An aqueous Triton-X100 (produced by Wako Pure Chemical Industries, Ltd.) solution was added to the tumor tissue and homogenated, and thereafter DMSO was added thereto to extract the dye, preparing a solution of the dye extracted. On the other hand, a tumor tissue was also resected from a tumor-bearing mouse to which nothing was administered, and an aqueous Triton-X100 solution was added thereto to prepare a tumor homogenate solution. Next, a known concentration of each polymer was diluted with the tumor homogenate solution to each concentration, and DMSO was added to the dilute solution to prepare a standard liquid for calibration, from which the dye was extracted. IVIS (registered trademark) Imaging System or Odyssey (registered trademark) CLx Infrared Imaging System (manufactured by LI-COR Biosciences) was used to measure the fluorescence intensity of each of the solution of the dye extracted and the standard liquid for calibration, thereby quantitatively determining the amount of the dye-conjugated polymer in the tumor tissue. The amount of the dye-conjugated polymer in tumor was expressed as % injected dose per weight of tumor tissue (% ID/g).

In the tumor accumulation property evaluation, blood was collected from the tail vein immediately before the mouse was euthanized by a carbon dioxide gas 10 or 24 hours after administration of the polymer of the present invention. The aqueous Triton-X100 solution was added to the blood collected, and DMSO was then added thereto to extract the dye, thereby preparing a blood solution of the dye extracted. On the other hand, a known concentration of the polymer of the present invention was diluted with the aqueous Triton-X100 solution to each concentration, and the solution diluted and the same amount of the blood collected from the mouse to which nothing was administered were mixed. Next, the aqueous Triton-X100 solution and DMSO were further added to the mixed solution with the blood to prepare a standard blood solution for calibration. IVIS (registered trademark) Imaging System or Odyssey (registered trademark) CLx Infrared Imaging System was used to measure the fluorescence intensity of each of the blood solution of the dye extracted and the standard blood solution for calibration, thereby quantitatively determining the amount of the dye-conjugated polymer in blood (% ID/g). The value obtained by dividing the amount of the dye-conjugated polymer in tumor (% ID/g) by the amount in blood (% ID/g) (hereinafter, abbreviated as the "tumor/blood ratio" or "T/B") was calculated. The results were summarized in Table 2 and Table 3. It was shown that the amount of PS1 in tumor was small both 10 and 24 hours after administration, and PS1 was not suitable for tumor imaging. On the other hand, it was confirmed that the amount of PS2, PS3 and PS4 in tumor was suitable for photoacoustic tumor imaging both 10 and 24 hours after administration, and the amount of PS2, PS3 and PS4 in tumor was increased according to an increase in the molecular weight of each of the polymers. It was shown that the tumor/blood ratio of PS2, PS3 and PS4 was more than 2 at each time point, and the photoacoustic signal from blood and the photoacoustic signal of a tumor site could be separated at a high contrast.

TABLE 2

| Polymer | Average molecular weight of PSAR portion | Amount in tumor at 10 hours after administration (% ID/g) | Amount in blood at 10 hours after administration (% ID/g) | Tumor/blood ratio |
|---|---|---|---|---|
| PS1 | 3800 | 2.7 ± 0.3 | 0.8 ± 0.1 | 3.3 ± 0.4 |
| PS2 | 6000 | 5.9 ± 1.2 | 1.1 ± 0.1 | 5.6 ± 0.8 |
| PS3 | 8000 | 6.4 ± 0.3 | 1.2 ± 0.5 | 5.4 ± 0.3 |
| PS4 | 26000 | 17.7 ± 5.1 | 7.0 ± 1.7 | 2.7 ± 0.2 |
| PEG1 | 20000 | 6.9 ± 1.3 | 13.3 ± 2.4 | 0.5 ± 0.1 |

TABLE 3

| Polymer | Average molecular weight of PSAR portion | Amount in tumor at 24 hours after administration (% ID/g) | Amount in blood at 24 hours after administration (% ID/g) | Tumor/blood ratio |
|---|---|---|---|---|
| PS1 | 3800 | 1.6 ± 0.8 | 0.5 ± 0.1 | 3.5 ± 1.6 |
| PS2 | 6000 | 4.9 ± 1.2 | 0.2 ± 0.1 | 36.1 ± 16.0 |
| PS3 | 8000 | 6.4 ± 1.5 | 0.03 ± 0.01 | 210 ± 48.5 |
| PS4 | 26000 | 14.3 ± 1.6 | 1.6 ± 0.2 | 9.4 ± 1.9 |
| PEG1 | 20000 | 15.8 ± 2.7 | 8.1 ± 0.9 | 1.7 ± 0.3 |

Comparative Example 1

(Conjugate of Polyethylene Glycol (PEG) and Dye)

PEG1 was comprised of PEG having a monoamino group at a terminal (ME-200EA (produced by NOF Corporation, weight average molecular weight: 20000)) and ICG-Sulfo-OSu. PEG1 was prepared according to a predetermined method. Binding of PEG and ICG was confirmed by electrophoresis. PEG1 prepared by the above method is represented by the following formula (Pg1), and $n_{14}$ represents an integer so that the average molecular weight of the PEG portion is 20000.

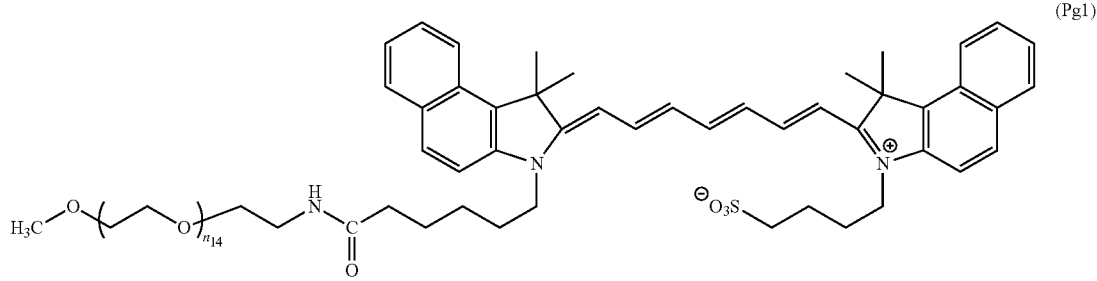

(Pg1)

Figure 2A:
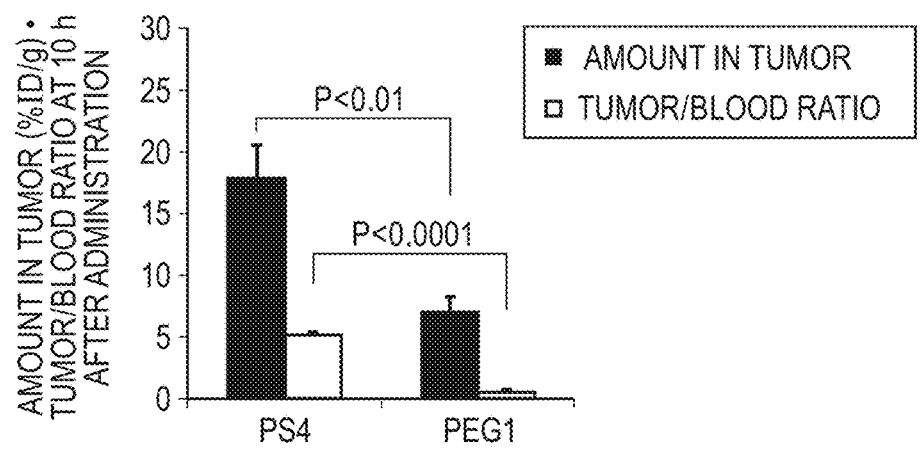
FIGS. 2A and 2B illustrate the amount in tumor and the tumor/blood ratio of both of polymer PS4 of the present invention and PEG1 of Comparative Example.
Figure 2B:
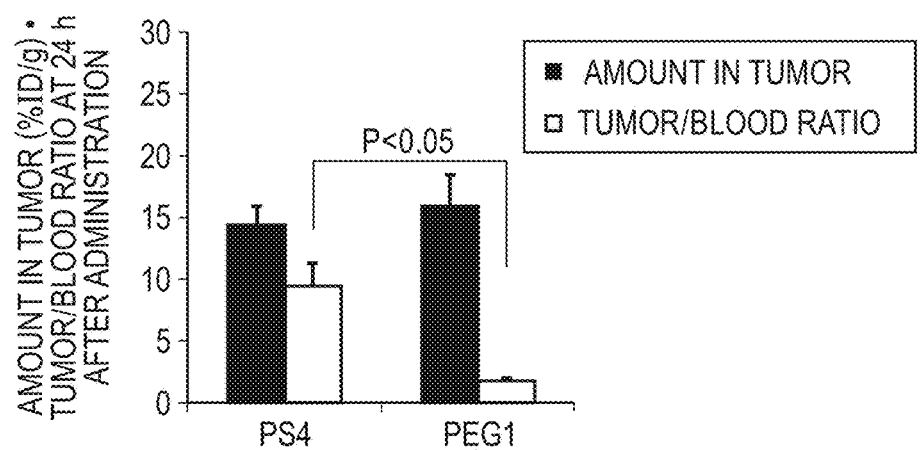

The amount of PEG1 in tumor and blood and the tumor/blood ratio of PEG1 were quantitatively determined by the same methods as in the polymer of the present invention, and summarized in Table 2 and Table 3. At 10 hours after administration, while the amount of PEG1 in tumor was large, the tumor/blood ratio was as low as 0.5. In addition, the tumor/blood ratio at 24 hours after administration was 1.7. Compared with PEG1, PS4 of the present invention exhibited a significantly high accumulation in tumor and a significantly high tumor/blood ratio at 10 hours after administration (FIG. 2A). Furthermore, PS4 also exhibited a significantly high tumor/blood ratio at 24 hours after administration (FIG. 2B). The significant test here was performed by the Student's t-test, and P<0.05 was determined as significant.

Example 4

(In Vivo Photoacoustic Tumor Imaging)

Figure 3A:
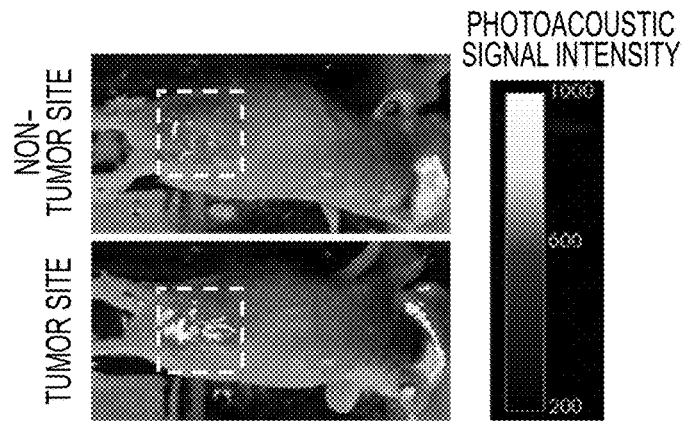
FIG. 3A illustrates superimposition of a photoacoustic signal image and a mouse whole-body picture of a tumor site and a non-tumor site at 10 hours after administration of polymer PS3 of the present invention.
Figure 3B:
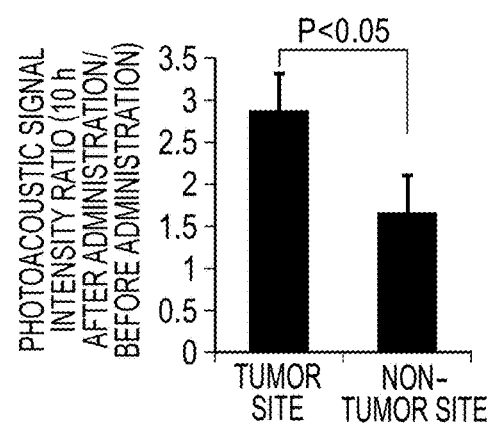
FIG. 3B illustrates the ratio of the photoacoustic signal intensity (10 hours after administration of polymer PS3 to before administration) of a tumor site and a non-tumor site.

In Examples of the present invention, the in vivo photoacoustic tumor imaging was performed using a photoacoustic imaging apparatus (Nexus128, produced by Endra Inc.). The tumor-bearing mouse prepared in the same manner as in the tumor accumulation property evaluation described above was put to sleep under anesthesia and then fixed to the imaging apparatus, and the photoacoustic signal was measured before and 10 hours after administration of the polymer of the present invention, to obtain each three-dimensional reconstruction data. The photoacoustic signal image was drawn with OsiriX Imaging Software using the three-dimensional reconstruction data obtained at 10 hours after administration, and superimposed with the mouse whole-body image (FIG. 3A). Furthermore, a region of interest (ROI) was set in a tumor region by GEHC MICROVIEW (manufactured by GE Healthcare), the photoacoustic signal intensity at each time was measured, and thereafter the ratio of the photoacoustic signal intensity at 10 hours after administration of the polymer of the present invention to the photoacoustic signal intensity before administration thereof was calculated (FIG. 3B). A significantly high photoacoustic signal was confirmed in the tumor-bearing mouse, to which polymer PS3 of the present invention was administered, at 10 hours after administration in a tumor site as compared with a non-tumor site (thigh), indicating the usefulness of the polymer of the present invention as a contrast agent for photoacoustic imaging.

Example 5

(Synthesis of Dye-Conjugated PSAR)

A polymerization reaction was performed in the same manner as in the method described in Example 1. Specifically, NPA as a polymerization initiator and super-dehydrated DMF as a reaction solvent were admixed with a monomer (NCA of SAR) in a Schlenk tube from which water was sufficiently removed and which was purged with a nitrogen gas, and the mixture was subjected to the reaction at room temperature. Table 4 shows the type of the polymerization initiator, the mixing ratio of the monomer to the polymerization initiator on a molar number basis at the initiation of the reaction, and the polymerization reaction time, in the polymerization reaction. The solution after the reaction was mixed with ice cooled diethyl ether, and PSAR precipitated was recovered by centrifugation (2000 rpm, 4° C., 15 minutes). The molecular weight of PSAR recovered was determined by using the GPC system described above, KD803 (manufactured by Showa Denko K.K.) as a column for analysis, and DMF as an eluent. PEG was used as a standard molecular weight substance for performing calibration. A solution of PSAR in DMF was allowed to flow into the column set at a flow rate of 1 ml/min at 40° C., and the molecular weight was calculated from the elution time. PSAR recovered was dissolved in 50 mM borate buffer (pH 8.6, 1 ml), ICG-Sulfo-OSu (1 mg/100 µl DMSO solution) was mixed therewith so that PSAR:ICG-Sulfo-OSu=1:1 was satisfied, and the reaction was performed under light shielding at room temperature for 24 hours. The solution after the reaction was dialyzed to methanol using Spectra/Por (registered trademark) 7 Dialysis Membrane (MWCO: 3.5 kDa), for purification. Binding of PSAR and ICG was confirmed by the absorbance and the weight, and it was found that about one ICG-Sulfo-OSu molecule was conjugated to one PSAR molecule in all of polymers PS5, PS6 and PS7 obtained. Furthermore, it was found from the analysis result by electrophoresis that 95% or more of ICG-Sulfo-OSu was covalently conjugated to PSAR. PS5, PS6 and PS7 obtained in the above method are represented by the formula (1), and $n_{11}$ represents an integer so that the average molecular weight of the PSAR portion is 8030 (PS5), 17540 (PS6) or 31500 (PS7).

TABLE 4

| Polymer | Type of polymerization initiator | Monomer/ polymerization initiator mixing ratio | Reaction time (hours) | Average molecular weight of PSAR portion |
|---------|----------------------------------|-----------------------------------------------|----------------------|------------------------------------------|
| PS5 | NPA | 140 | 110 | 8030 |
| PS6 | NPA | 280 | 110 | 17540 |
| PS7 | NPA | 420 | 110 | 31500 |

Example 6

(Biodistribution Study)

Figure 4:
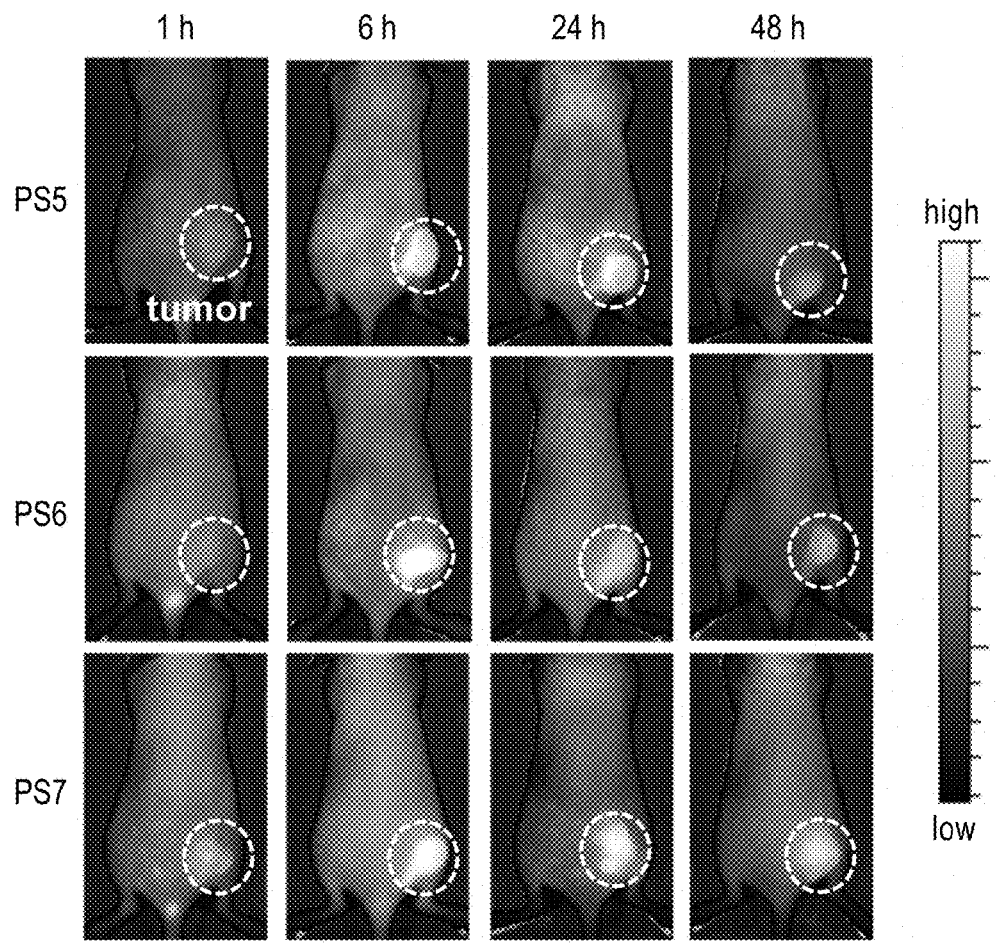
FIG. 4 illustrates whole-body fluorescence images of tumor-bearing mice at 1, 6, 24 and 48 hours after administration of polymers PS5, PS6 and PS7 of the present invention.

The biodistribution of each of polymers PS5, PS6 and PS7 was evaluated by the same method as in Example 3. Specifically, the polymer of the present invention was administered (an amount of the dye of 5 nmol) to a Colon26 tumor-bearing mouse, and fluorescence imaging of the tumor-bearing mouse at 1, 6, 24 and 48 hours after the administration was performed by IVIS (registered trademark) Imaging System. The results obtained by taking whole-body fluorescence images of respective mice to which polymers PS5, PS6 and PS7 were administered were illustrated in FIG. 4. Strong fluorescence was observed from polymers PS5, PS6 and PS7 accumulated in a tumor.

Figure 5A:
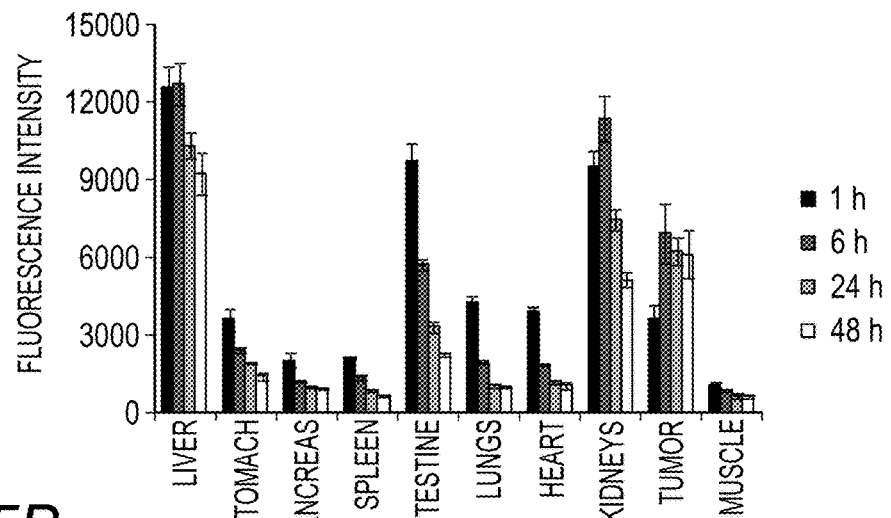
FIGS. 5A, 5B and 5C illustrate the fluorescence intensities of organs of tumor-bearing mice at 1, 6, 24 and 48 hours after administration of polymers PS5, PS6 and PS7, respectively.
Figure 5B:
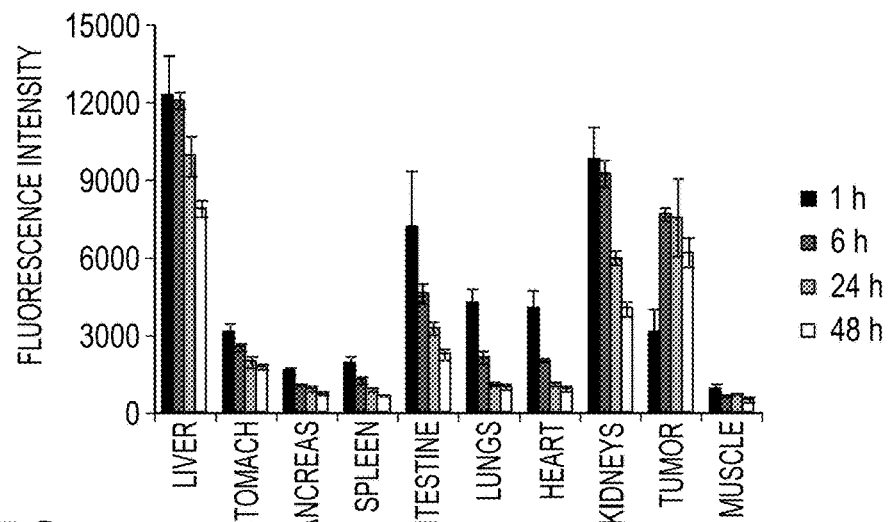
Figure 5C:
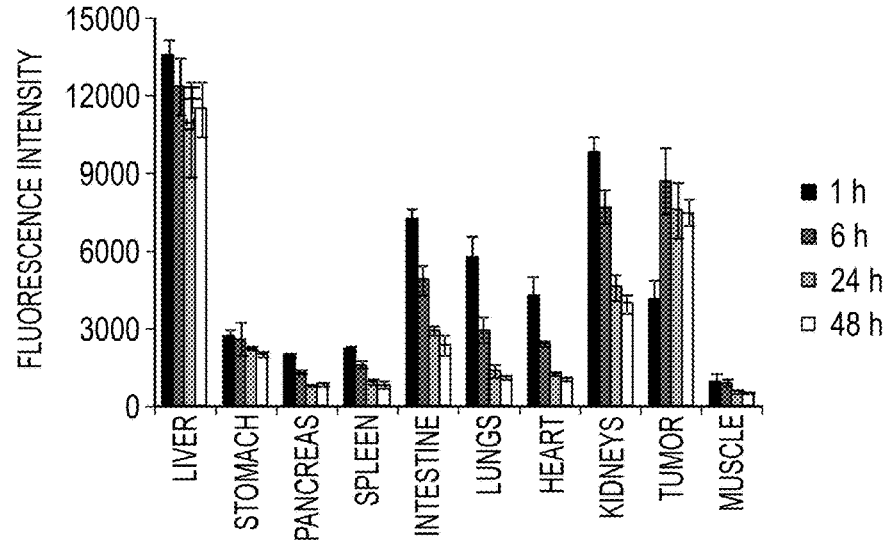

Subsequently, respective tumor-bearing mice to which polymers PS5, PS6 and PS7 were administered were euthanized at 1, 6, 24 and 48 hours after administration, main organs were resected, and fluorescence imaging was performed. The results were summarized in FIGS. 5A to 5C. Strong fluorescence was observed from a tumor in all of the polymers. In addition to the illustration in FIGS. 5A to 5C, relatively strong fluorescence was observed in the liver and the kidneys.

Figure 6A:
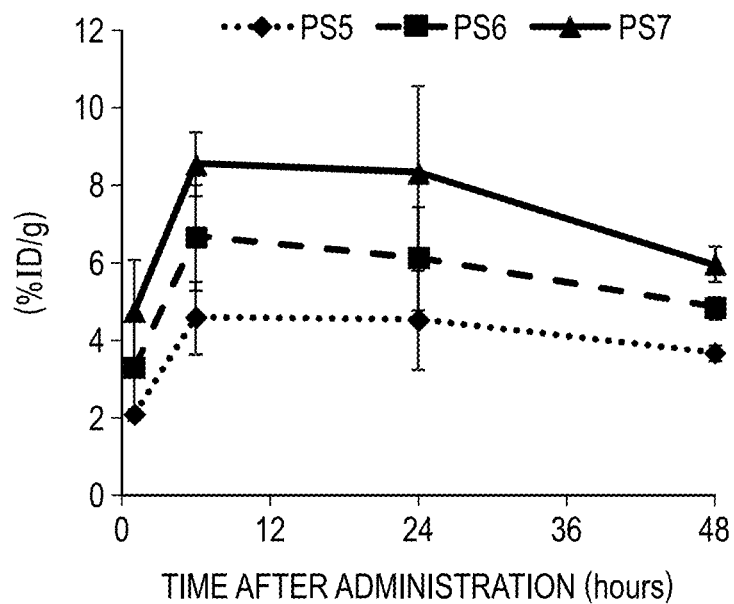
FIGS. 6A and 6B illustrate time-dependent changes of the amount in tumor and blood of polymers PS5, PS6 and PS7 administered to tumor-bearing mice, respectively.
Figure 6B:
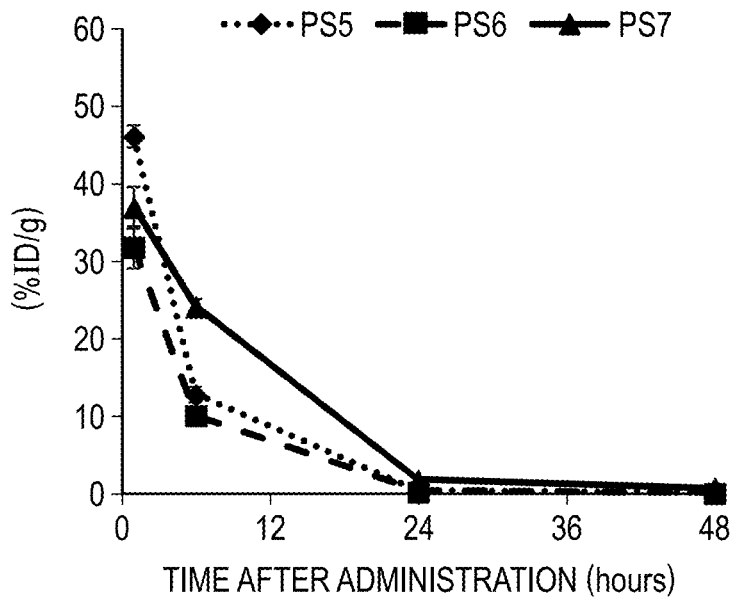

The amount of each polymer PS5, PS6 and PS7 in tumor and blood at each time point and the tumor/blood ratio at 24 hours after administration were determined by the above methods. The results were summarized in FIG. 6A, FIG. 6B and Table 5. Consequently, polymer PS7 was more accumulated in a tumor than PS5 and PS6. The time until each polymer excreted from blood was extended as the molecular weight of the polymer was increased. The tumor/blood ratio at 24 hours after administration was more than 2 in PS5, PS6 and PS7, indicating that the photoacoustic signal of a tumor site could be distinguished at a high contrast.

TABLE 5

| Polymer | Average molecular weight of PSAR portion | Amount in tumor at 24 hours after administration (% ID/g) | Amount in blood at 24 hours after administration (% ID/g) | Tumor/blood ratio |
|---------|------------------------------------------|-----------------------------------------------------------|-----------------------------------------------------------|-------------------|
| PS5 | 8030 | 4.6 ± 1.3 | 0.3 ± 0.02 | 14.1 ± 4.0 |
| PS6 | 17540 | 6.2 ± 1.3 | 0.4 ± 0.03 | 17.3 ± 2.7 |

TABLE 5-continued

| Polymer | Average molecular weight of PSAR portion | Amount in tumor at 24 hours after administration (% ID/g) | Amount in blood at 24 hours after administration (% ID/g) | Tumor/blood ratio |
|---------|------------------------------------------|-----------------------------------------------------------|-----------------------------------------------------------|-------------------|
| PS7 | 31500 | 8.4 ± 2.3 | 1.8 ± 0.4 | 4.6 ± 1.3 |
| PEG2 | 30000 | 13.1 ± 2.1 | 21.6 ± 4.0 | 0.6 ± 0.02 |

Comparative Example 2

(Conjugate of Polyethylene Glycol (PEG) and Dye)

Polymer PEG2 was comprised of PEG having a mono-amino group at a terminal (ME-300EA (produced by NOF Corporation, weight average molecular weight: 30000)) and ICG-Sulfo-OSu. PEG2 was prepared according to a predetermined method. Binding of PEG and ICG was confirmed by electrophoresis. PEG2 prepared by the above method is represented by the formula (Pg1), and $n_{14}$ represents an integer so that the average molecular weight of the PEG portion is 30000.

The amount of PEG2 in tumor and blood and the tumor/blood ratio of PEG2 were quantitatively determined by the same methods as in Example 6, and summarized in Table 5. At 24 hours after administration of PEG2, while the amount of PEG2 in tumor was large, the tumor/blood ratio was as low as 0.6. Compared with PEG2, polymer PS7 exhibited a significantly higher tumor/blood ratio at 24 hours after administration. The significant test here was performed by the Student's t-test, and P<0.05 was determined as significant.

Example 7

(Cellular Uptake Experiment)

Figure 7A:
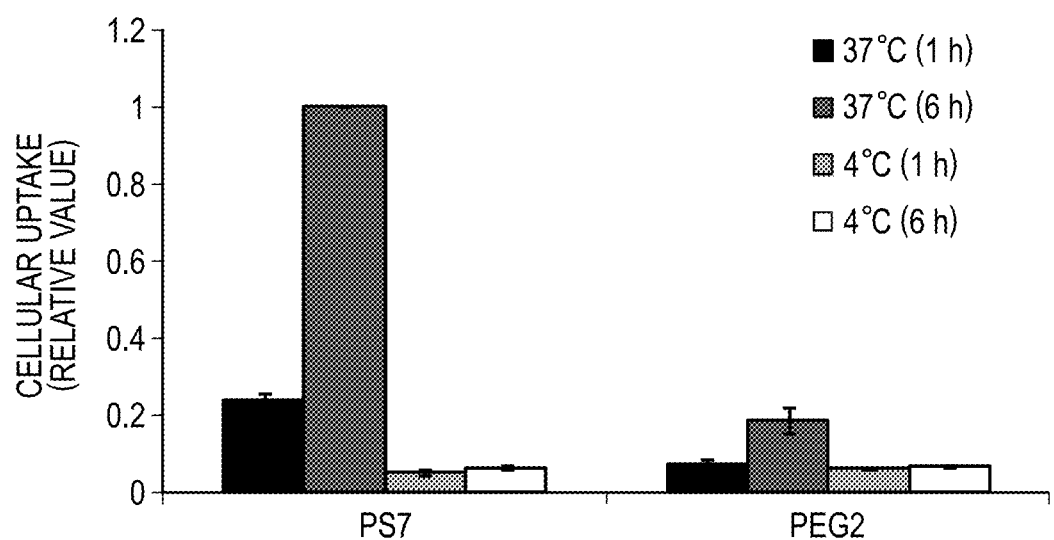
FIGS. 7A and 7B illustrate cellular uptake study of polymer PS7 and PEG2 of Comparative Example.

Cellular uptake evaluation of polymer PS7 and PEG2 prepared in Comparative Example 2 was performed by fluorescence measurement. Colon26 cells were cultured in a 6-well plate for 2 days. Thereafter, each of polymer PS7 and PEG2 (each 500 µM ICG) was added to a medium, and cultured at 37° C. for 1 hour or 6 hours. Subsequently, the resultant was washed with Phosphate Buffer Saline (hereinafter, sometimes abbreviated as "PBS"), and the cells were recovered. Fluorescence measurement of the cell mass was performed in IVIS (registered trademark) Imaging System, and the fluorescence intensity determined was corrected by the number of the cells. The above cellular uptake experiment was performed in the same manner even in a condition of 4° C. in order to evaluate involvement of an active transport mechanism. The experiment was performed by use of DMEM (10% FBS, 25 mM HEPES) as a culture liquid. The results were summarized in FIG. 7A.

When culturing was performed at 37° C. for 1 hour or 6 hours, the fluorescence intensity from the cell mass to which polymer PS7 was added was significantly high as compared with the fluorescence intensity as the result of PEG2 (P<0.001). The significant test here was performed by the Student's t-test. The fluorescence intensity of PS7 was considerably reduced (94%) in the case of culturing at 4° C.

Figure 7B:
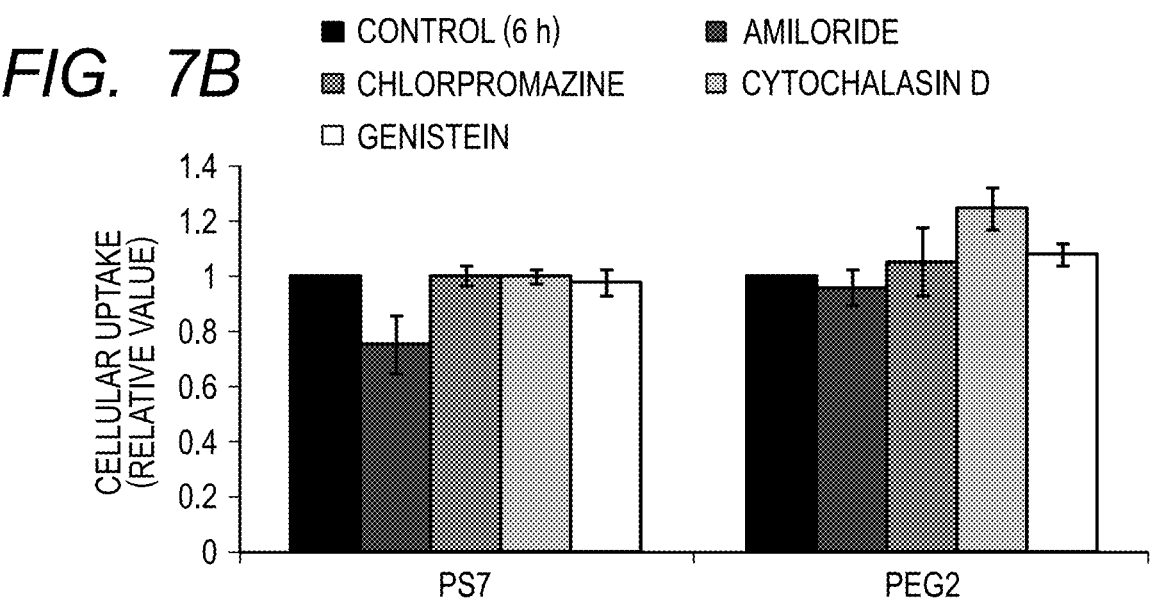

Subsequently, in order to examine the cellular uptake mechanism of each of polymer PS7 and PEG2, cellular uptake was evaluated using an endocytosis inhibitor. Amiloride (micropinocytosis inhibitor, 1 mM), genistein (caveolae-mediated endocytosis inhibitor, 200 µM), chlorpromazine (clathrin-mediated endocytosis inhibitor, 7 µM) and cytochalasin D (phagocytosis inhibitor, 5 µM) were each added as the endocytosis inhibitor to Colon26 cells cultured in a 6-well plate for 2 days. Each polymer PS7 and PEG2 (each 500 µM ICG) was added and the cells were cultured for 1 or 6 hours. A case where no inhibitor was added and culturing was performed for the same time was used as control. Subsequently, the resultant was washed with PBS, and the cells were recovered. Fluorescence measurement of the cell mass was performed by the above method, and the results were summarized in FIG. 7B. It was found that cellular uptake of PS7 was significantly inhibited by amiloride among the four endocytosis inhibitors (P<0.05). The significant test here was performed by the Student's t-test.

Example 8

(Protein Binding Experiment)

Polymer PS7 of the present invention (0 to 60 µM), PEG2 prepared in Comparative Example 2 (0 to 60 µM) or PSAR having an average molecular weight of 31500 (PS7 to which no ICG was conjugated, 0 to 60 µM) was mixed with a bovine serum albumin (BSA, 2 µM) solution. After 30 minutes, the fluorescence intensity derived from tryptophan of BSA was measured by a spectrofluorophotometer (RF-5300PC, manufactured by Shimadzu Corporation) (excitation wavelength: 279 nm, fluorescence wavelength: 342 nm). The binding affinity of BSA and each compound was calculated by the Hill equation represented by the following equation (1).

$$\log [(F_0-F)/F] = \log K_b + n \log C \quad (1)$$

In the equation (1), $K_b$ represents the binding constant, n represents the number of binding sites, F and $F_0$ represent the fluorescence intensities derived from tryptophan of BSA with and without each compound, respectively, and C represents the concentration of each compound added. The results were as follows. PSAR having an average molecular weight of 31500 did not interact with BSA. On the other hand, polymer PS7 and PEG2 were each weakly bound to BSA. The $K_b$ values of polymer PS7 and PEG2 were $0.40 \times 10^5$ M$^{-1}$ and $0.44 \times 10^5$ M$^{-1}$, respectively.

Example 9

(In Vivo Photoacoustic Tumor Imaging)

Figure 8:
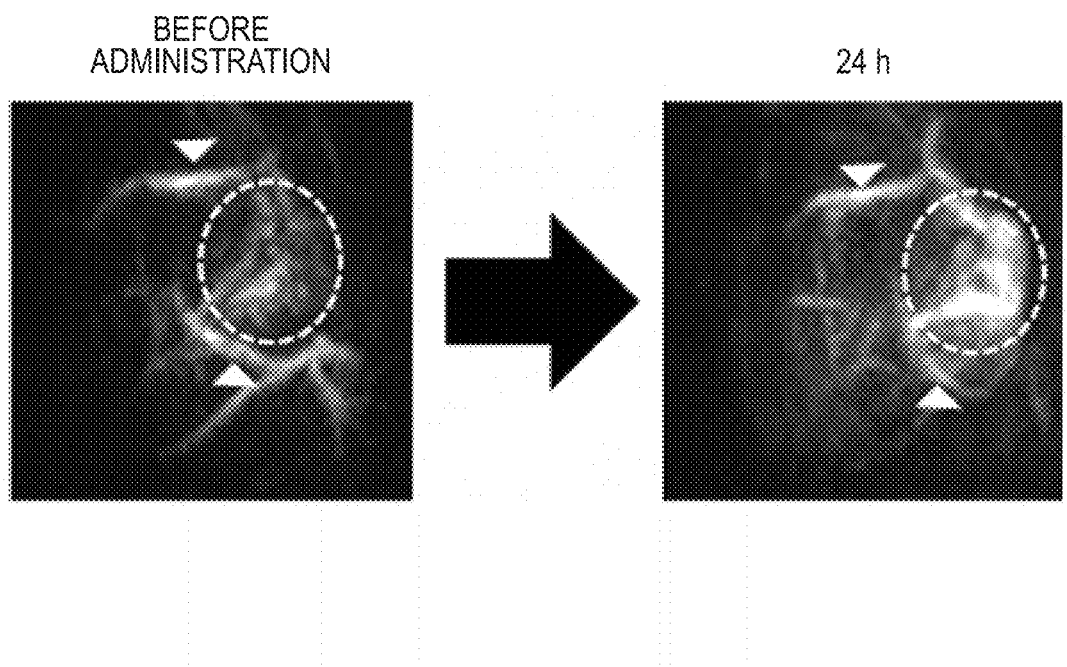
FIG. 8 illustrates photoacoustic signal images of a tumor site before and 24 hours after administration of polymer PS7.

Polymer PS7 was used to perform the in vivo photoacoustic tumor imaging in the same manner as in Example 4. Specifically, the tumor-bearing mouse prepared in the same manner as in Example 3 was put to sleep under anesthesia, and then fixed to the imaging apparatus, and the photoacoustic signal was measured before and 24 hours after administration of PS7 (40 nmol ICG) to obtain each three-dimensional reconstruction data. The photoacoustic signal image was drawn with OsiriX Imaging Software using the obtained three-dimensional reconstruction data, and the results were illustrated in FIG. 8. Furthermore, a region of interest (ROI) was set in a tumor region by freely available medical image analysis software AMIDE, the photoacoustic signal intensity at each time was measured, and thereafter the ratio of the photoacoustic signal intensity at 24 hours after administration of PS7 to the photoacoustic signal intensity before administration was calculated. The photoacoustic signal was increased 2.5 times in a tumor site at 24 hours after administration of PS7, and a tumor could be clearly visualized. Furthermore, because of high tumor/blood ratio of PS7, high contrast PA images in which blood vessel (indicated by the arrows in FIG. 8) showed low PA signal was obtained. These results indicated the usefulness of the polymer of the present invention as a contrast agent for photoacoustic imaging.

Advantageous Effects of Invention

The polymer according to the present invention, the main chain of which has a structure of polysarcosine, is thus accumulated in a tumor, and excreted from blood with the lapse of time, and therefore can be high in the tumor/blood ratio to be used for a contrast agent that enable us to detect a tumor selectively.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-194334, filed Sep. 30, 2015, and Japanese Patent Application No. 2016-022505, filed Feb. 9, 2016, which are hereby incorporated by reference herein in their entirety.

The invention claimed is:

1. A polymer represented by formula (1) or (2):

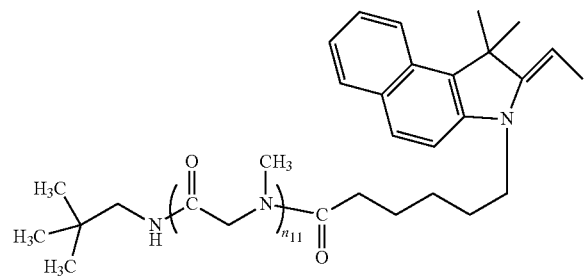

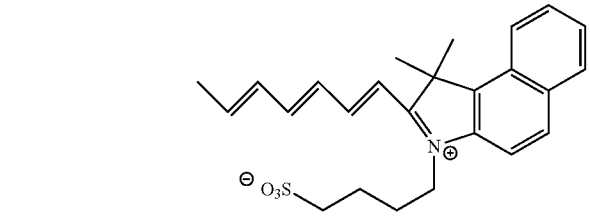

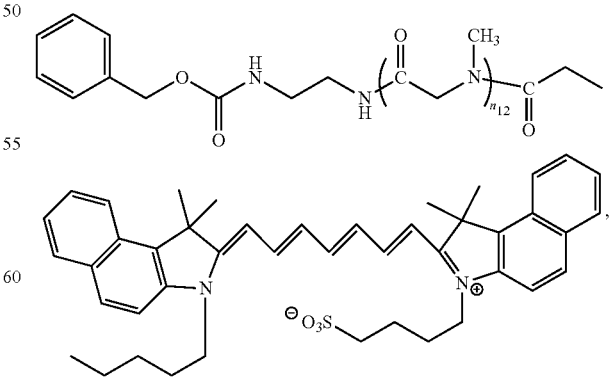

wherein each of n11 and n12 represents an integer of 180 or more.

2. The polymer according to claim 1, wherein an average molecular weight of the polymer is 13000 to 100000.

3. The polymer according to claim 1, wherein an average molecular weight of the polymer is 13000 to 50000.

4. A contrast agent for photoacoustic imaging, comprising:
the polymer according to claim 1; and
a dispersion medium.

5. A polymer represented by formula (1) or (2):

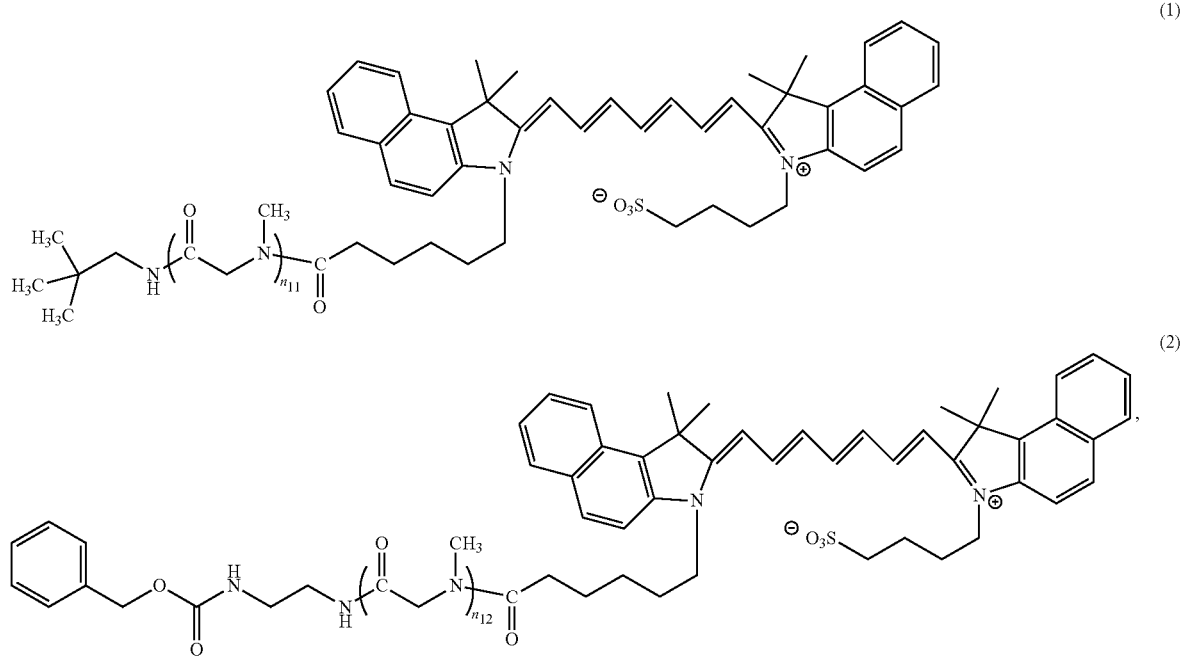

wherein each of n11 and n12 represents an integer of 110 or more.

6. A contrast agent for photoacoustic imaging, comprising: the polymer according to claim 5; and a dispersion medium.

* * * * *